(12) United States Patent
Spivey et al.

(10) Patent No.: US 7,815,662 B2
(45) Date of Patent: Oct. 19, 2010

(54) SURGICAL SUTURE ANCHORS AND DEPLOYMENT DEVICE

(75) Inventors: James T. Spivey, Cincinnati, OH (US); David Stefanchik, Morrow, OH (US); Christopher Paul Swain, London (GB)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 570 days.

(21) Appl. No.: 11/715,710

(22) Filed: Mar. 8, 2007

(65) Prior Publication Data

US 2008/0221619 A1  Sep. 11, 2008

(51) Int. Cl.
*A61B 17/04* (2006.01)
*A61B 17/08* (2006.01)
(52) U.S. Cl. .................. 606/232; 606/151; 24/129 R
(58) Field of Classification Search ............ 606/232, 606/151, 157, 158; 24/115 R, 132 R, 133, 24/136 R, 132 AA, 136 A, 129 R
See application file for complete search history.

(56) References Cited

U.S. PATENT DOCUMENTS

| 1,127,948 | A | | 2/1915 | Wappler |
|---|---|---|---|---|
| 2,028,635 | A | | 1/1936 | Wappler |
| 2,113,246 | A | | 4/1938 | Wappler |
| 2,196,620 | A | * | 4/1940 | Attarian ............... 43/44.85 |
| 2,952,206 | A | * | 9/1960 | Becksted ............ 102/275.7 |
| 3,470,876 | A | | 10/1969 | Barchilon |
| 3,994,301 | A | | 11/1976 | Agris |
| 4,011,872 | A | | 3/1977 | Komiya |
| 4,012,812 | A | * | 3/1977 | Black ..................... 24/114.3 |
| 4,178,920 | A | | 12/1979 | Cawood, Jr. et al. |
| 4,207,873 | A | | 6/1980 | Kruy |
| 4,235,238 | A | | 11/1980 | Ogiu et al. |

(Continued)

FOREIGN PATENT DOCUMENTS

DE    3008120 A1    9/1980

(Continued)

OTHER PUBLICATIONS

International Search Report for PCT/US2008/055840, Jan. 5, 2009 (9 pages).

(Continued)

*Primary Examiner*—Julian W Woo
*Assistant Examiner*—Christopher L Templeton

(57) ABSTRACT

A suture anchor is provided which includes a hollow member having an outer surface defining an enclosure, the member having a longitudinal axis and a slot through a portion of the outer surface in a direction transverse to the longitudinal axis, the slot providing an opening into the enclosure. The suture anchor further includes a one-way valve positioned within the enclosure at the slot to allow entry of a suture through the slot into the enclosure and to prevent the exit of the suture from the enclosure. A device is provided for deploying the suture anchor. The deployment device includes an elongate hollow member having a suture anchor release zone positioned at the distal end, a launch bar having at least a portion positioned in the release zone. The launch bar is movable within the release zone between a resting position and a launching position and is operatively connected to an actuation member positioned proximally to the elongate member. The hollow elongate member defines a housing for receiving a plurality of suture anchors in tandem.

6 Claims, 9 Drawing Sheets

U.S. PATENT DOCUMENTS

| | | |
|---|---|---|
| 4,258,716 A | 3/1981 | Sutherland |
| 4,278,077 A | 7/1981 | Mizumoto |
| 4,285,344 A | 8/1981 | Marshall |
| 4,311,143 A | 1/1982 | Komiya |
| 4,396,021 A | 8/1983 | Baumgartner |
| 4,452,246 A | 6/1984 | Bader et al. |
| 4,461,281 A | 7/1984 | Carson |
| 4,491,132 A | 1/1985 | Aikins |
| 4,527,331 A | 7/1985 | Lasner et al. |
| 4,538,594 A | 9/1985 | Boebel et al. |
| D281,104 S | 10/1985 | Davison |
| 4,580,551 A | 4/1986 | Siegmund et al. |
| 4,646,722 A | 3/1987 | Silverstein et al. |
| 4,653,476 A | 3/1987 | Bonnet |
| 4,669,470 A | 6/1987 | Brandfield |
| 4,685,447 A | 8/1987 | Iversen et al. |
| 4,711,240 A | 12/1987 | Goldwasser et al. |
| 4,712,545 A | 12/1987 | Honkanen |
| D295,894 S | 5/1988 | Sharkany et al. |
| 4,763,669 A | 8/1988 | Jaeger |
| 4,770,188 A | 9/1988 | Chikama |
| 4,823,794 A * | 4/1989 | Pierce .................. 606/232 |
| 4,829,999 A * | 5/1989 | Auth ....................... 606/1 |
| 4,873,979 A | 10/1989 | Hanna |
| 4,880,015 A | 11/1989 | Nierman |
| 4,911,148 A | 3/1990 | Sosnowski et al. |
| 4,926,860 A | 5/1990 | Stice et al. |
| 4,938,214 A | 7/1990 | Specht et al. |
| 4,950,273 A | 8/1990 | Briggs |
| 4,950,285 A * | 8/1990 | Wilk ..................... 606/232 |
| 4,984,581 A | 1/1991 | Stice |
| 5,020,514 A | 6/1991 | Heckele |
| 5,020,535 A | 6/1991 | Parker et al. |
| 5,025,778 A | 6/1991 | Silverstein et al. |
| 5,033,169 A * | 7/1991 | Bindon .................. 24/129 R |
| 5,037,433 A | 8/1991 | Wilk et al. |
| 5,041,129 A | 8/1991 | Hayhurst et al. |
| 5,046,513 A | 9/1991 | Gatturna et al. |
| 5,050,585 A | 9/1991 | Takahashi |
| 5,065,516 A | 11/1991 | Dulebohn |
| 5,066,295 A | 11/1991 | Kozak et al. |
| 5,123,913 A * | 6/1992 | Wilk et al. ............. 606/232 |
| 5,123,914 A | 6/1992 | Cope |
| 5,133,727 A | 7/1992 | Bales et al. |
| 5,174,300 A | 12/1992 | Bales et al. |
| 5,176,126 A | 1/1993 | Chikama |
| 5,190,555 A | 3/1993 | Wetter et al. |
| 5,192,284 A | 3/1993 | Pleatman |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,219,357 A | 6/1993 | Honkanen et al. |
| 5,219,358 A | 6/1993 | Bendel et al. |
| 5,234,453 A | 8/1993 | Smith et al. |
| 5,235,964 A | 8/1993 | Abenaim |
| 5,246,424 A | 9/1993 | Wilk |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,284,128 A | 2/1994 | Hart |
| 5,290,302 A | 3/1994 | Pericic |
| 5,295,977 A | 3/1994 | Cohen et al. |
| 5,297,536 A | 3/1994 | Wilk |
| 5,312,416 A | 5/1994 | Spaeth et al. |
| 5,320,636 A | 6/1994 | Slater |
| 5,325,845 A | 7/1994 | Adair |
| 5,330,471 A | 7/1994 | Eggers |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,198 A | 8/1994 | Hart et al. |
| 5,344,428 A | 9/1994 | Griffiths |
| 5,350,391 A | 9/1994 | Iacovelli |
| 5,352,184 A | 10/1994 | Goldberg et al. |
| 5,352,222 A | 10/1994 | Rydell |
| 5,354,311 A | 10/1994 | Kambin et al. |
| 5,356,408 A | 10/1994 | Rydell |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,370,647 A | 12/1994 | Graber et al. |
| 5,374,273 A | 12/1994 | Nakao et al. |
| 5,383,877 A | 1/1995 | Clarke |
| 5,383,888 A | 1/1995 | Zvenyatsky et al. |
| 5,392,789 A | 2/1995 | Slater et al. |
| 5,395,386 A | 3/1995 | Slater |
| 5,401,248 A | 3/1995 | Bencini |
| 5,403,342 A | 4/1995 | Tovey et al. |
| 5,403,348 A | 4/1995 | Bonutti |
| 5,405,073 A | 4/1995 | Porter |
| 5,405,359 A | 4/1995 | Pierce |
| 5,433,721 A | 7/1995 | Hooven et al. |
| 5,439,471 A | 8/1995 | Kerr |
| 5,439,478 A | 8/1995 | Palmer |
| 5,441,059 A | 8/1995 | Dannan |
| 5,449,021 A | 9/1995 | Chikama |
| 5,456,684 A | 10/1995 | Schmidt et al. |
| 5,458,131 A | 10/1995 | Wilk |
| 5,458,583 A | 10/1995 | McNeely et al. |
| 5,460,168 A | 10/1995 | Masubuchi et al. |
| 5,465,731 A | 11/1995 | Bell et al. |
| 5,467,763 A | 11/1995 | McMahon et al. |
| 5,468,250 A | 11/1995 | Paraschac et al. |
| 5,470,308 A | 11/1995 | Edwards et al. |
| 5,470,320 A | 11/1995 | Tiefenbrun et al. |
| 5,478,347 A | 12/1995 | Aranyi |
| 5,480,404 A | 1/1996 | Kammerer et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,992 A | 3/1996 | Meade et al. |
| 5,503,616 A | 4/1996 | Jones |
| 5,505,686 A | 4/1996 | Willis et al. |
| 5,511,564 A | 4/1996 | Wilk |
| 5,514,157 A | 5/1996 | Nicholas et al. |
| 5,522,829 A | 6/1996 | Michalos |
| 5,522,830 A | 6/1996 | Aranyi |
| 5,554,151 A | 9/1996 | Hinchliffe |
| 5,558,133 A * | 9/1996 | Bortoli et al. ............... 139/448 |
| 5,562,693 A | 10/1996 | Devlin et al. |
| 5,569,243 A | 10/1996 | Kortenbach et al. |
| 5,569,298 A | 10/1996 | Schnell |
| 5,578,030 A | 11/1996 | Levin |
| 5,582,611 A | 12/1996 | Tsuruta et al. |
| 5,582,617 A | 12/1996 | Klieman et al. |
| 5,584,845 A | 12/1996 | Hart |
| 5,593,420 A | 1/1997 | Eubanks, Jr et al. |
| 5,595,562 A | 1/1997 | Grier |
| 5,597,378 A | 1/1997 | Jervis |
| 5,601,573 A | 2/1997 | Fogelberg et al. |
| 5,601,588 A | 2/1997 | Tonomura et al. |
| 5,604,531 A | 2/1997 | Iddan et al. |
| 5,607,389 A | 3/1997 | Edwards et al. |
| 5,607,450 A | 3/1997 | Zvenyatsky et al. |
| 5,618,303 A | 4/1997 | Marlow et al. |
| 5,624,399 A | 4/1997 | Ackerman |
| 5,628,732 A | 5/1997 | Antoon, Jr. et al. |
| 5,630,782 A | 5/1997 | Adair |

| | | | | | | |
|---|---|---|---|---|---|---|
| 5,643,283 A | 7/1997 | Younker | | 5,957,953 A | 9/1999 | DiPoto et al. |
| 5,643,294 A | 7/1997 | Tovey et al. | | 5,971,995 A | 10/1999 | Rousseau |
| 5,645,083 A | 7/1997 | Essig et al. | | 5,976,074 A | 11/1999 | Moriyama |
| 5,649,372 A | 7/1997 | Souza | | 5,976,075 A | 11/1999 | Beane et al. |
| 5,653,677 A | 8/1997 | Okada et al. | | 5,976,130 A | 11/1999 | McBrayer et al. |
| 5,662,663 A | 9/1997 | Shallman | | 5,980,556 A | 11/1999 | Giordano et al. |
| 5,669,875 A | 9/1997 | van Eerdenburg | | 5,984,938 A | 11/1999 | Yoon |
| 5,681,324 A | 10/1997 | Kammerer et al. | | 5,989,182 A | 11/1999 | Hori et al. |
| 5,681,330 A | 10/1997 | Hughett et al. | | 5,993,447 A | 11/1999 | Blewett et al. |
| 5,685,820 A | 11/1997 | Riek et al. | | 6,001,120 A | 12/1999 | Levin |
| 5,695,448 A | 12/1997 | Kimura et al. | | 6,004,330 A | 12/1999 | Middleman et al. |
| 5,695,511 A | 12/1997 | Cano et al. | | 6,007,566 A * | 12/1999 | Wenstrom, Jr. ............ 606/232 |
| 5,709,708 A * | 1/1998 | Thal ............................ 606/232 | | 6,010,515 A | 1/2000 | Swain et al. |
| 5,730,740 A | 3/1998 | Wales et al. | | 6,019,770 A | 2/2000 | Christoudias |
| 5,741,278 A | 4/1998 | Stevens | | 6,024,708 A | 2/2000 | Bales et al. |
| 5,741,285 A | 4/1998 | McBrayer et al. | | 6,027,522 A | 2/2000 | Palmer |
| 5,746,759 A | 5/1998 | Meade et al. | | 6,030,365 A | 2/2000 | Laufer |
| 5,749,889 A | 5/1998 | Bacich et al. | | 6,033,399 A | 3/2000 | Gines |
| 5,752,951 A | 5/1998 | Yanik | | 6,053,927 A | 4/2000 | Hamas |
| 5,766,167 A | 6/1998 | Eggers et al. | | 6,066,160 A * | 5/2000 | Colvin et al. ............... 606/232 |
| 5,766,170 A | 6/1998 | Eggers | | 6,068,629 A | 5/2000 | Haissaguerre et al. |
| 5,766,205 A | 6/1998 | Zvenyatsky et al. | | 6,071,233 A | 6/2000 | Ishikawa et al. |
| 5,769,849 A | 6/1998 | Eggers | | 6,090,108 A | 7/2000 | McBrayer et al. |
| 5,779,701 A | 7/1998 | McBrayer et al. | | 6,096,046 A | 8/2000 | Weiss |
| 5,779,716 A | 7/1998 | Cano et al. | | 6,110,183 A | 8/2000 | Cope |
| 5,779,727 A | 7/1998 | Orejola | | 6,139,555 A | 10/2000 | Hart et al. |
| 5,782,866 A * | 7/1998 | Wenstrom, Jr. ............ 606/232 | | 6,149,653 A * | 11/2000 | Deslauriers ................. 606/232 |
| 5,791,022 A * | 8/1998 | Bohman ...................... 24/130 | | 6,149,662 A | 11/2000 | Pugliesi et al. |
| 5,792,113 A | 8/1998 | Kramer et al. | | 6,159,200 A | 12/2000 | Verdura et al. |
| 5,792,153 A | 8/1998 | Swain et al. | | 6,165,184 A | 12/2000 | Verdura et al. |
| 5,792,165 A | 8/1998 | Klieman et al. | | 6,168,605 B1 | 1/2001 | Measamer et al. |
| 5,797,835 A | 8/1998 | Green | | 6,170,130 B1 * | 1/2001 | Hamilton et al. .......... 24/115 R |
| 5,797,928 A | 8/1998 | Kogasaka | | 6,179,776 B1 | 1/2001 | Adams et al. |
| 5,797,939 A | 8/1998 | Yoon | | 6,179,837 B1 | 1/2001 | Hooven |
| 5,797,941 A | 8/1998 | Schulze et al. | | 6,190,384 B1 | 2/2001 | Ouchi |
| 5,803,903 A | 9/1998 | Athas et al. | | 6,203,533 B1 | 3/2001 | Ouchi |
| 5,808,665 A | 9/1998 | Green | | 6,206,872 B1 | 3/2001 | Lafond et al. |
| 5,810,806 A | 9/1998 | Ritchart et al. | | 6,206,877 B1 | 3/2001 | Kese et al. |
| 5,810,865 A | 9/1998 | Koscher et al. | | 6,261,242 B1 | 7/2001 | Roberts et al. |
| 5,810,876 A | 9/1998 | Kelleher | | 6,264,664 B1 | 7/2001 | Avellanet |
| 5,810,877 A | 9/1998 | Roth et al. | | 6,270,497 B1 | 8/2001 | Sekino et al. |
| 5,813,976 A | 9/1998 | Filipi et al. | | 6,277,136 B1 | 8/2001 | Bonutti |
| 5,814,058 A | 9/1998 | Carlson et al. | | 6,283,963 B1 | 9/2001 | Regula |
| 5,817,061 A | 10/1998 | Goodwin et al. | | 6,293,909 B1 | 9/2001 | Chu et al. |
| 5,817,107 A | 10/1998 | Schaller | | 6,293,952 B1 | 9/2001 | Brosens et al. |
| 5,817,119 A | 10/1998 | Klieman et al. | | 6,322,578 B1 | 11/2001 | Houle et al. |
| 5,819,736 A | 10/1998 | Avny et al. | | 6,326,177 B1 | 12/2001 | Schoenbach et al. |
| 5,827,281 A | 10/1998 | Levin | | 6,350,267 B1 | 2/2002 | Stefanchik |
| 5,830,231 A | 11/1998 | Geiges, Jr. | | 6,352,503 B1 | 3/2002 | Matsui et al. |
| 5,833,700 A | 11/1998 | Fogelberg et al. | | 6,355,035 B1 | 3/2002 | Manushakian |
| 5,833,703 A | 11/1998 | Manushakian | | 6,371,956 B1 | 4/2002 | Wilson et al. |
| 5,843,017 A | 12/1998 | Yoon | | 6,379,366 B1 | 4/2002 | Fleischman et al. |
| 5,849,022 A | 12/1998 | Sakashita et al. | | 6,383,195 B1 | 5/2002 | Richard |
| 5,853,374 A | 12/1998 | Hart et al. | | 6,383,197 B1 | 5/2002 | Conlon et al. |
| 5,860,913 A | 1/1999 | Yamaya et al. | | 6,391,029 B1 | 5/2002 | Hooven et al. |
| 5,860,995 A | 1/1999 | Berkelaar | | 6,406,440 B1 | 6/2002 | Stefanchik |
| 5,882,331 A | 3/1999 | Sasaki | | 6,409,733 B1 | 6/2002 | Conlon et al. |
| 5,882,344 A | 3/1999 | Stouder, Jr. | | 6,431,500 B1 * | 8/2002 | Jacobs et al. .................. 248/51 |
| 5,893,846 A | 4/1999 | Bales et al. | | 6,447,511 B1 | 9/2002 | Slater |
| 5,893,874 A | 4/1999 | Bourque et al. | | 6,447,523 B1 | 9/2002 | Middleman et al. |
| 5,893,875 A | 4/1999 | O'Connor et al. | | 6,454,783 B1 | 9/2002 | Piskun |
| 5,899,919 A | 5/1999 | Eubanks, Jr. et al. | | 6,454,785 B2 | 9/2002 | De Hoyos Garza |
| 5,908,420 A | 6/1999 | Parins et al. | | 6,464,701 B1 | 10/2002 | Hooven et al. |
| 5,916,147 A | 6/1999 | Boury | | 6,475,104 B1 | 11/2002 | Lutz et al. |
| 5,921,997 A | 7/1999 | Fogelberg et al. | | 6,485,411 B1 | 11/2002 | Konstorum et al. |
| 5,922,008 A | 7/1999 | Gimpelson | | 6,491,626 B1 | 12/2002 | Stone et al. |
| 5,925,052 A | 7/1999 | Simmons | | 6,491,691 B1 | 12/2002 | Morley et al. |
| 5,928,255 A | 7/1999 | Meade et al. | | 6,494,893 B2 | 12/2002 | Dubrul et al. |
| 5,944,718 A | 8/1999 | Austin et al. | | 6,503,192 B1 | 1/2003 | Ouchi |
| 5,951,549 A | 9/1999 | Richardson et al. | | 6,506,190 B1 | 1/2003 | Walshe |
| 5,954,720 A | 9/1999 | Wilson et al. | | 6,508,827 B1 | 1/2003 | Manhes |
| 5,954,731 A | 9/1999 | Yoon | | 6,543,456 B1 | 4/2003 | Freeman |
| 5,957,943 A | 9/1999 | Vaitekunas | | 6,551,270 B1 | 4/2003 | Bimbo et al. |

| | | |
|---|---|---|
| 6,554,829 B2 | 4/2003 | Schulze et al. |
| 6,558,384 B2 | 5/2003 | Mayenberger |
| 6,562,035 B1 | 5/2003 | Levin |
| 6,569,159 B1 | 5/2003 | Edwards et al. |
| 6,572,629 B2 | 6/2003 | Kalloo et al. |
| 6,572,635 B1 | 6/2003 | Bonutti |
| 6,575,988 B2 | 6/2003 | Rousseau |
| 6,592,559 B1 | 7/2003 | Pakter et al. |
| 6,592,603 B2 | 7/2003 | Lasner |
| 6,605,105 B1 | 8/2003 | Cuschieri et al. |
| 6,626,919 B1 | 9/2003 | Swanstrom |
| 6,632,229 B1 | 10/2003 | Yamanouchi |
| 6,652,521 B2 | 11/2003 | Schulze |
| 6,652,551 B1 | 11/2003 | Heiss |
| 6,663,641 B1 | 12/2003 | Kovac et al. |
| 6,666,854 B1 | 12/2003 | Lange |
| 6,672,338 B1 | 1/2004 | Esashi et al. |
| 6,673,087 B1 | 1/2004 | Chang et al. |
| 6,685,628 B2 | 2/2004 | Vu |
| 6,692,445 B2 | 2/2004 | Roberts et al. |
| 6,692,462 B2 | 2/2004 | Mackenzie et al. |
| 6,699,180 B2 | 3/2004 | Kobayashi |
| 6,699,256 B1 | 3/2004 | Logan et al. |
| 6,699,263 B2 | 3/2004 | Cope |
| 6,716,226 B2 | 4/2004 | Sixto, Jr. et al. |
| 6,740,030 B2 | 5/2004 | Martone et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,811 B2 | 6/2004 | Chu et al. |
| 6,752,822 B2 | 6/2004 | Jespersen |
| 6,761,685 B2 | 7/2004 | Adams et al. |
| 6,773,434 B2 | 8/2004 | Ciarrocca |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,864 B2 | 9/2004 | Matsuura et al. |
| 6,790,173 B2 | 9/2004 | Saadat et al. |
| 6,800,056 B2 | 10/2004 | Tartaglia et al. |
| 6,808,491 B2 | 10/2004 | Kortenbach et al. |
| 6,824,548 B2 | 11/2004 | Smith et al. |
| 6,837,847 B2 | 1/2005 | Ewers et al. |
| 6,843,794 B2 | 1/2005 | Sixto, Jr. et al. |
| 6,861,250 B1 | 3/2005 | Cole et al. |
| 6,878,110 B2 | 4/2005 | Yang et al. |
| 6,884,213 B2 | 4/2005 | Raz et al. |
| 6,887,255 B2 | 5/2005 | Shimm |
| 6,896,683 B1 | 5/2005 | Gadberry et al. |
| 6,908,476 B2 | 6/2005 | Jud et al. |
| 6,918,871 B2 | 7/2005 | Schulze |
| 6,932,810 B2 | 8/2005 | Ryan |
| 6,932,827 B2 | 8/2005 | Cole |
| 6,942,613 B2 | 9/2005 | Ewers et al. |
| 6,945,979 B2 | 9/2005 | Kortenbach et al. |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,962,587 B2 | 11/2005 | Johnson et al. |
| 6,964,662 B2 | 11/2005 | Kidooka |
| 6,966,909 B2 | 11/2005 | Marshall et al. |
| 6,967,462 B1 | 11/2005 | Landis |
| 6,971,988 B2 | 12/2005 | Orban, III |
| 6,972,017 B2 | 12/2005 | Smith et al. |
| 6,976,992 B2 | 12/2005 | Sachatello et al. |
| 6,984,205 B2 | 1/2006 | Gazdzinski |
| 6,986,774 B2 | 1/2006 | Middleman et al. |
| 6,988,987 B2 | 1/2006 | Ishikawa et al. |
| 6,991,627 B2 | 1/2006 | Madhani et al. |
| 6,994,708 B2 | 2/2006 | Manzo |
| 6,997,931 B2 | 2/2006 | Sauer et al. |
| 7,008,375 B2 | 3/2006 | Weisel |
| 7,009,634 B2 | 3/2006 | Iddan et al. |
| 7,010,340 B2 | 3/2006 | Scarantino et al. |
| 7,029,438 B2 | 4/2006 | Morin et al. |
| 7,041,052 B2 | 5/2006 | Saadat et al. |
| 7,052,489 B2 | 5/2006 | Griego et al. |
| 7,060,024 B2 | 6/2006 | Long et al. |
| 7,060,025 B2 | 6/2006 | Long et al. |
| 7,063,697 B2 | 6/2006 | Slater |
| 7,066,879 B2 | 6/2006 | Fowler et al. |
| 7,066,936 B2 | 6/2006 | Ryan |
| 7,070,602 B2 | 7/2006 | Smith et al. |
| 7,076,305 B2 | 7/2006 | Imran et al. |
| 7,083,629 B2 | 8/2006 | Weller et al. |
| 7,087,071 B2 | 8/2006 | Nicholas et al. |
| 7,090,673 B2 | 8/2006 | Dycus et al. |
| 7,090,685 B2 | 8/2006 | Kortenbach et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,112,208 B2 | 9/2006 | Morris et al. |
| 7,118,531 B2 | 10/2006 | Krill |
| 7,118,587 B2 | 10/2006 | Dycus et al. |
| 7,128,708 B2 | 10/2006 | Saadat et al. |
| RE39,415 E | 11/2006 | Bales et al. |
| 7,131,978 B2 | 11/2006 | Sancoff et al. |
| 7,137,980 B2 | 11/2006 | Buysse et al. |
| 7,137,981 B2 | 11/2006 | Long |
| 7,147,650 B2 | 12/2006 | Lee |
| 7,153,321 B2 | 12/2006 | Andrews |
| 7,163,525 B2 | 1/2007 | Franer |
| 7,172,714 B2 | 2/2007 | Jacobson |
| 7,179,254 B2 | 2/2007 | Pendekmanti et al. |
| 7,195,612 B2 | 3/2007 | Van Sloten et al. |
| 7,195,631 B2 | 3/2007 | Dumbauld |
| 7,208,005 B2 | 4/2007 | Frecker et al. |
| 7,223,272 B2 | 5/2007 | Francese et al. |
| 7,232,445 B2 | 6/2007 | Kortenbach et al. |
| 7,241,290 B2 | 7/2007 | Doyle et al. |
| 7,244,228 B2 | 7/2007 | Lubowski |
| 7,252,660 B2 | 8/2007 | Kunz |
| 7,270,663 B2 | 9/2007 | Nakao |
| 7,306,597 B2 | 12/2007 | Manzo |
| 7,329,257 B2 | 2/2008 | Kanehira et al. |
| 7,329,383 B2 | 2/2008 | Stinson |
| 7,344,536 B1 | 3/2008 | Lunsford et al. |
| 7,364,582 B2 | 4/2008 | Lee |
| 7,402,162 B2 | 7/2008 | Ouchi |
| 7,422,590 B2 | 9/2008 | Kupferschmid et al. |
| 7,488,295 B2 | 2/2009 | Burbank et al. |
| 7,497,867 B2 | 3/2009 | Lasner et al. |
| 7,524,281 B2 * | 4/2009 | Chu et al. ............ 600/37 |
| 7,544,203 B2 | 6/2009 | Chin et al. |
| 7,579,550 B2 | 8/2009 | Dayton et al. |
| 2001/0049497 A1 | 12/2001 | Kalloo et al. |
| 2002/0022857 A1 | 2/2002 | Goldsteen et al. |
| 2002/0023353 A1 | 2/2002 | Ting-Kung |
| 2002/0068945 A1 | 6/2002 | Sixto, Jr. et al. |
| 2002/0078967 A1 | 6/2002 | Sixto, Jr. et al. |
| 2002/0082516 A1 | 6/2002 | Stefanchik |
| 2002/0091391 A1 | 7/2002 | Cole et al. |
| 2002/0107530 A1 | 8/2002 | Sauer et al. |
| 2002/0138086 A1 | 9/2002 | Sixto, Jr. et al. |
| 2002/0147456 A1 | 10/2002 | Diduch et al. |
| 2002/0183591 A1 | 12/2002 | Matsuura et al. |
| 2003/0036679 A1 | 2/2003 | Kortenbach et al. |
| 2003/0114732 A1 | 6/2003 | Webler et al. |
| 2003/0130564 A1 | 7/2003 | Martone et al. |
| 2003/0130656 A1 | 7/2003 | Levin |
| 2003/0167062 A1 * | 9/2003 | Gambale et al. ............ 606/138 |
| 2003/0171651 A1 | 9/2003 | Page et al. |
| 2003/0176880 A1 | 9/2003 | Long et al. |
| 2003/0191497 A1 | 10/2003 | Cope |
| 2003/0195565 A1 | 10/2003 | Bonutti |

| | | | | | | |
|---|---|---|---|---|---|---|
| 2003/0216611 A1 | 11/2003 | Vu | | 2005/0277952 A1 | 12/2005 | Arp et al. |
| 2003/0216615 A1 | 11/2003 | Ouchi | | 2005/0277954 A1 | 12/2005 | Smith et al. |
| 2003/0225312 A1 | 12/2003 | Suzuki et al. | | 2005/0277955 A1 | 12/2005 | Palmer et al. |
| 2003/0229269 A1 | 12/2003 | Humphrey | | 2005/0277956 A1 | 12/2005 | Francese et al. |
| 2003/0229371 A1 | 12/2003 | Whitworth | | 2005/0277957 A1 | 12/2005 | Kuhns et al. |
| 2003/0236549 A1 | 12/2003 | Bonadio et al. | | 2005/0283118 A1 | 12/2005 | Uth et al. |
| 2004/0002735 A1 | 1/2004 | Lizardi et al. | | 2005/0288555 A1 | 12/2005 | Binmoeller |
| 2004/0098007 A1 | 5/2004 | Heiss | | 2006/0004406 A1 | 1/2006 | Wehrstein et al. |
| 2004/0116948 A1 | 6/2004 | Sixto, Jr. et al. | | 2006/0004409 A1 | 1/2006 | Nobis et al. |
| 2004/0133089 A1 | 7/2004 | Kilcoyne et al. | | 2006/0004410 A1 | 1/2006 | Nobis et al. |
| 2004/0138525 A1 | 7/2004 | Saadat et al. | | 2006/0015009 A1 | 1/2006 | Jaffe et al. |
| 2004/0138529 A1 | 7/2004 | Wiltshire et al. | | 2006/0020167 A1 | 1/2006 | Sitzmann |
| 2004/0138587 A1 | 7/2004 | Lyons, IV | | 2006/0020247 A1 | 1/2006 | Kagan et al. |
| 2004/0186350 A1 | 9/2004 | Brenneman et al. | | 2006/0025654 A1 | 2/2006 | Suzuki et al. |
| 2004/0193146 A1 | 9/2004 | Lee et al. | | 2006/0025819 A1 | 2/2006 | Nobis et al. |
| 2004/0193186 A1 | 9/2004 | Kortenbach et al. | | 2006/0041188 A1 | 2/2006 | Dirusso et al. |
| 2004/0193188 A1 | 9/2004 | Francese | | 2006/0058582 A1 | 3/2006 | Maahs et al. |
| 2004/0193189 A1 | 9/2004 | Kortenbach et al. | | 2006/0058776 A1 | 3/2006 | Bilsbury |
| 2004/0193200 A1 | 9/2004 | Dworschak et al. | | 2006/0079890 A1 | 4/2006 | Guerra |
| 2004/0199052 A1 | 10/2004 | Banik et al. | | 2006/0089528 A1 | 4/2006 | Tartaglia et al. |
| 2004/0210245 A1 | 10/2004 | Erickson et al. | | 2006/0095060 A1 | 5/2006 | Mayenberger et al. |
| 2004/0215058 A1 | 10/2004 | Zirps et al. | | 2006/0106423 A1* | 5/2006 | Weisel et al. ................ 606/232 |
| 2004/0225186 A1 | 11/2004 | Horne, Jr. et al. | | 2006/0111209 A1 | 5/2006 | Hinman et al. |
| 2004/0230095 A1 | 11/2004 | Stefanchik et al. | | 2006/0129166 A1 | 6/2006 | Lavelle |
| 2004/0230096 A1 | 11/2004 | Stefanchik et al. | | 2006/0135971 A1 | 6/2006 | Swanstrom et al. |
| 2004/0230097 A1 | 11/2004 | Stefanchik et al. | | 2006/0135984 A1 | 6/2006 | Kramer et al. |
| 2004/0249367 A1 | 12/2004 | Saadat et al. | | 2006/0142644 A1 | 6/2006 | Mulac et al. |
| 2004/0249394 A1 | 12/2004 | Morris et al. | | 2006/0142790 A1 | 6/2006 | Gertner |
| 2005/0033277 A1 | 2/2005 | Clague et al. | | 2006/0149132 A1 | 7/2006 | Iddan |
| 2005/0033333 A1 | 2/2005 | Smith et al. | | 2006/0149135 A1 | 7/2006 | Paz |
| 2005/0049616 A1 | 3/2005 | Rivera et al. | | 2006/0161190 A1 | 7/2006 | Gadberry et al. |
| 2005/0065397 A1 | 3/2005 | Saadat et al. | | 2006/0167416 A1 | 7/2006 | Mathis et al. |
| 2005/0065517 A1 | 3/2005 | Chin | | 2006/0167482 A1 | 7/2006 | Swain et al. |
| 2005/0070754 A1 | 3/2005 | Nobis et al. | | 2006/0178560 A1 | 8/2006 | Saadat et al. |
| 2005/0070763 A1 | 3/2005 | Nobis et al. | | 2006/0183975 A1 | 8/2006 | Saadat et al. |
| 2005/0070764 A1 | 3/2005 | Nobis et al. | | 2006/0189844 A1 | 8/2006 | Tien |
| 2005/0080413 A1 | 4/2005 | Canady | | 2006/0189845 A1 | 8/2006 | Maahs et al. |
| 2005/0090837 A1 | 4/2005 | Sixto, Jr. et al. | | 2006/0190027 A1 | 8/2006 | Downey |
| 2005/0090838 A1 | 4/2005 | Sixto, Jr. et al. | | 2006/0195084 A1 | 8/2006 | Slater |
| 2005/0101837 A1 | 5/2005 | Kalloo et al. | | 2006/0200005 A1 | 9/2006 | Bjork et al. |
| 2005/0101838 A1 | 5/2005 | Camillocci et al. | | 2006/0200169 A1 | 9/2006 | Sniffin |
| 2005/0107664 A1 | 5/2005 | Kalloo et al. | | 2006/0200170 A1 | 9/2006 | Aranyi |
| 2005/0110881 A1 | 5/2005 | Glukhovsky et al. | | 2006/0200199 A1 | 9/2006 | Bonutti et al. |
| 2005/0113847 A1 | 5/2005 | Gadberry et al. | | 2006/0217697 A1 | 9/2006 | Lau et al. |
| 2005/0124855 A1 | 6/2005 | Jaffe et al. | | 2006/0217742 A1 | 9/2006 | Messerly et al. |
| 2005/0125010 A1 | 6/2005 | Smith et al. | | 2006/0217743 A1 | 9/2006 | Messerly et al. |
| 2005/0131279 A1 | 6/2005 | Boulais et al. | | 2006/0229639 A1 | 10/2006 | Whitfield |
| 2005/0131457 A1 | 6/2005 | Douglas et al. | | 2006/0229640 A1 | 10/2006 | Whitfield |
| 2005/0137454 A1 | 6/2005 | Saadat et al. | | 2006/0237022 A1 | 10/2006 | Chen et al. |
| 2005/0143690 A1 | 6/2005 | High | | 2006/0237023 A1 | 10/2006 | Cox et al. |
| 2005/0143774 A1 | 6/2005 | Polo | | 2006/0253004 A1 | 11/2006 | Frisch et al. |
| 2005/0149087 A1 | 7/2005 | Ahlberg et al. | | 2006/0253039 A1 | 11/2006 | McKenna et al. |
| 2005/0149096 A1 | 7/2005 | Hilal et al. | | 2006/0258907 A1 | 11/2006 | Stefanchik et al. |
| 2005/0159648 A1 | 7/2005 | Freed | | 2006/0258908 A1 | 11/2006 | Stefanchik et al. |
| 2005/0165378 A1 | 7/2005 | Heinrich et al. | | 2006/0258910 A1 | 11/2006 | Stefanchik et al. |
| 2005/0165411 A1 | 7/2005 | Orban, III | | 2006/0258954 A1 | 11/2006 | Timberlake et al. |
| 2005/0165429 A1 | 7/2005 | Douglas et al. | | 2006/0258955 A1 | 11/2006 | Hoffman et al. |
| 2005/0192598 A1 | 9/2005 | Johnson et al. | | 2006/0259010 A1 | 11/2006 | Stefanchik et al. |
| 2005/0192602 A1 | 9/2005 | Manzo | | 2006/0264752 A1 | 11/2006 | Rubinsky et al. |
| 2005/0209624 A1 | 9/2005 | Vijay | | 2006/0264930 A1 | 11/2006 | Nishimura |
| 2005/0215858 A1 | 9/2005 | Vail, III | | 2006/0271102 A1 | 11/2006 | Bosshard et al. |
| 2005/0216050 A1 | 9/2005 | Sepetka et al. | | 2006/0276835 A1 | 12/2006 | Uchida |
| 2005/0228406 A1 | 10/2005 | Bose | | 2006/0285732 A1 | 12/2006 | Horn et al. |
| 2005/0234297 A1 | 10/2005 | Devierre et al. | | 2006/0287644 A1 | 12/2006 | Inganas et al. |
| 2005/0250990 A1 | 11/2005 | Le et al. | | 2006/0287666 A1 | 12/2006 | Saadat et al. |
| 2005/0251176 A1 | 11/2005 | Swanstrom et al. | | 2007/0002135 A1 | 1/2007 | Glukhovsky |
| 2005/0261674 A1 | 11/2005 | Nobis et al. | | 2007/0015965 A1 | 1/2007 | Cox et al. |
| 2005/0267492 A1 | 12/2005 | Poncet et al. | | 2007/0016225 A1 | 1/2007 | Nakao |
| 2005/0272975 A1 | 12/2005 | McWeeney et al. | | 2007/0032700 A1 | 2/2007 | Fowler et al. |
| 2005/0272977 A1 | 12/2005 | Saadat et al. | | 2007/0032701 A1 | 2/2007 | Fowler et al. |
| 2005/0273084 A1 | 12/2005 | Hinman et al. | | 2007/0049800 A1 | 3/2007 | Boulais |
| 2005/0277945 A1 | 12/2005 | Saadat et al. | | 2007/0051375 A1 | 3/2007 | Milliman |
| 2005/0277951 A1 | 12/2005 | Smith et al. | | 2007/0079924 A1 | 4/2007 | Saadat et al. |

| | | | | | | |
|---|---|---|---|---|---|---|
| 2007/0100376 A1 | 5/2007 | Mikkaichi et al. | | 2009/0192344 A1 | 7/2009 | Bakos et al. |
| 2007/0106118 A1 | 5/2007 | Moriyama | | 2009/0227828 A1 | 9/2009 | Swain et al. |
| 2007/0112342 A1 | 5/2007 | Pearson et al. | | 2009/0248055 A1 | 10/2009 | Spivey et al. |
| 2007/0112383 A1 | 5/2007 | Conlon et al. | | 2009/0281559 A1 | 11/2009 | Swain et al. |
| 2007/0112384 A1 | 5/2007 | Conlon et al. | | 2009/0287236 A1 | 11/2009 | Bakos et al. |
| 2007/0112385 A1 | 5/2007 | Conlon | | 2009/0299135 A1 | 12/2009 | Spivey |
| 2007/0118115 A1 | 5/2007 | Artale et al. | | 2009/0299143 A1 | 12/2009 | Conlon et al. |
| 2007/0123840 A1 | 5/2007 | Cox | | 2009/0299362 A1 | 12/2009 | Long et al. |
| 2007/0129719 A1 | 6/2007 | Kendale et al. | | 2009/0299385 A1 | 12/2009 | Stefanchik et al. |
| 2007/0135709 A1 | 6/2007 | Rioux et al. | | 2009/0299406 A1 | 12/2009 | Swain et al. |
| 2007/0156127 A1 | 7/2007 | Rioux et al. | | 2009/0299409 A1 | 12/2009 | Coe et al. |
| 2007/0173869 A1 | 7/2007 | Gannoe et al. | | 2009/0306658 A1 | 12/2009 | Nobis et al. |
| 2007/0173870 A2 | 7/2007 | Zacharias | | 2009/0306683 A1 | 12/2009 | Zwolinski et al. |
| 2007/0179525 A1 | 8/2007 | Frecker et al. | | 2009/0326561 A1 | 12/2009 | Carroll, II et al. |
| 2007/0179530 A1* | 8/2007 | Tieu et al. .................. 606/232 | | 2010/0010294 A1 | 1/2010 | Conlon et al. |
| 2007/0203487 A1 | 8/2007 | Sugita | | 2010/0010298 A1 | 1/2010 | Bakos et al. |
| 2007/0213754 A1 | 9/2007 | Mikkaichi et al. | | 2010/0010299 A1 | 1/2010 | Bakos et al. |
| 2007/0225554 A1 | 9/2007 | Maseda et al. | | 2010/0010303 A1 | 1/2010 | Bakos |
| 2007/0244358 A1 | 10/2007 | Lee | | 2010/0010511 A1 | 1/2010 | Harris et al. |
| 2007/0250057 A1 | 10/2007 | Nobis et al. | | | | |
| 2007/0255096 A1 | 11/2007 | Stefanchik et al. | | FOREIGN PATENT DOCUMENTS | | |
| 2007/0255100 A1 | 11/2007 | Barlow et al. | | | | |
| 2007/0255273 A1 | 11/2007 | Fernandez et al. | | DE | 19757056 B4 | 8/2008 |
| 2007/0255306 A1 | 11/2007 | Conlon et al. | | EP | 0086338 A1 | 8/1983 |
| 2007/0260112 A1 | 11/2007 | Rahmani | | EP | 0464479 B1 | 3/1995 |
| 2007/0260117 A1 | 11/2007 | Zwolinski et al. | | EP | 0724863 B1 | 7/1999 |
| 2007/0260273 A1 | 11/2007 | Cropper et al. | | EP | 0760629 B1 | 11/1999 |
| 2007/0270629 A1 | 11/2007 | Charles | | EP | 0818974 B1 | 7/2001 |
| 2007/0270889 A1 | 11/2007 | Conlon et al. | | EP | 0947166 B1 | 5/2003 |
| 2007/0270907 A1 | 11/2007 | Stokes et al. | | EP | 0836832 B1 | 12/2003 |
| 2007/0282371 A1 | 12/2007 | Lee et al. | | EP | 1402837 A1 | 3/2004 |
| 2008/0004650 A1 | 1/2008 | George | | EP | 0744918 B1 | 4/2004 |
| 2008/0015409 A1 | 1/2008 | Barlow et al. | | EP | 0931515 B1 | 8/2004 |
| 2008/0015552 A1 | 1/2008 | Doyle et al. | | EP | 1411843 B1 | 10/2004 |
| 2008/0027387 A1 | 1/2008 | Grabinsky | | EP | 1150614 B1 | 11/2004 |
| 2008/0086172 A1 | 4/2008 | Martin et al. | | EP | 1477104 A1 | 11/2004 |
| 2008/0097483 A1 | 4/2008 | Ortiz et al. | | EP | 1481642 A1 | 12/2004 |
| 2008/0103527 A1 | 5/2008 | Martin et al. | | EP | 1493391 A1 | 1/2005 |
| 2008/0119870 A1 | 5/2008 | Williams | | EP | 0848598 B1 | 2/2005 |
| 2008/0125796 A1 | 5/2008 | Graham | | EP | 1281360 B1 | 3/2005 |
| 2008/0132892 A1 | 6/2008 | Lunsford et al. | | EP | 1568330 A1 | 8/2005 |
| 2008/0147113 A1 | 6/2008 | Nobis et al. | | EP | 1452143 B1 | 9/2005 |
| 2008/0171907 A1 | 7/2008 | Long et al. | | EP | 1616527 A2 | 1/2006 |
| 2008/0200755 A1 | 8/2008 | Bakos | | EP | 1006888 B1 | 3/2006 |
| 2008/0200762 A1 | 8/2008 | Stokes et al. | | EP | 1013229 B1 | 6/2006 |
| 2008/0200911 A1 | 8/2008 | Long | | EP | 1721561 A1 | 11/2006 |
| 2008/0200912 A1 | 8/2008 | Long | | EP | 1153578 B1 | 3/2007 |
| 2008/0200933 A1 | 8/2008 | Bakos et al. | | EP | 1334696 B1 | 3/2007 |
| 2008/0200934 A1 | 8/2008 | Fox | | EP | 1769766 A1 | 4/2007 |
| 2008/0228213 A1 | 9/2008 | Blakeney et al. | | EP | 1836971 A2 | 9/2007 |
| 2008/0243106 A1 | 10/2008 | Coe et al. | | EP | 1857061 A1 | 11/2007 |
| 2008/0269782 A1 | 10/2008 | Stefanchik et al. | | EP | 1875876 A1 | 1/2008 |
| 2008/0269783 A1 | 10/2008 | Griffith | | EP | 1518499 B1 | 8/2008 |
| 2008/0275474 A1 | 11/2008 | Martin et al. | | EP | 1994904 A1 | 11/2008 |
| 2008/0275475 A1 | 11/2008 | Schwemberger et al. | | EP | 1707130 B1 | 12/2008 |
| 2008/0300547 A1 | 12/2008 | Bakos | | EP | 1769749 B1 | 11/2009 |
| 2008/0312496 A1 | 12/2008 | Zwolinski | | FR | 2731610 A1 | 9/1996 |
| 2008/0312506 A1 | 12/2008 | Spivey et al. | | GB | 2403909 A | 1/2005 |
| 2009/0054728 A1 | 2/2009 | Trusty | | JP | 2002-369791 A | 12/2002 |
| 2009/0062788 A1 | 3/2009 | Long et al. | | JP | 2003-088494 A | 3/2003 |
| 2009/0062792 A1 | 3/2009 | Vakharia et al. | | JP | 2003-235852 A | 8/2003 |
| 2009/0062795 A1 | 3/2009 | Vakharia et al. | | JP | 2004-065745 A | 3/2004 |
| 2009/0112059 A1 | 4/2009 | Nobis | | JP | 2005-121947 A | 5/2005 |
| 2009/0112062 A1 | 4/2009 | Bakos | | JP | 2005-261514 A | 9/2005 |
| 2009/0112063 A1 | 4/2009 | Bakos et al. | | SU | 194230 | 5/1967 |
| 2009/0131751 A1 | 5/2009 | Spivey et al. | | SU | 980703 | 12/1982 |
| 2009/0131932 A1 | 5/2009 | Vakharia et al. | | WO | WO 92/13494 A1 | 8/1992 |
| 2009/0131933 A1 | 5/2009 | Ghabrial et al. | | WO | WO 93/10850 A1 | 6/1993 |
| 2009/0143639 A1 | 6/2009 | Stark | | WO | WO 93/20760 A1 | 10/1993 |
| 2009/0143794 A1 | 6/2009 | Conlon et al. | | WO | WO 93/20765 A1 | 10/1993 |
| 2009/0149710 A1 | 6/2009 | Stefanchik et al. | | WO | WO 95/09666 A1 | 4/1995 |
| 2009/0177219 A1 | 7/2009 | Conlon | | WO | WO 96/22056 A1 | 7/1996 |
| 2009/0182332 A1 | 7/2009 | Long et al. | | WO | WO 96/27331 A1 | 9/1996 |

| | | |
|---|---|---|
| WO | WO 96/39946 A1 | 12/1996 |
| WO | WO 97/12557 A1 | 4/1997 |
| WO | WO 99/09919 A1 | 3/1999 |
| WO | WO 99/17661 A1 | 4/1999 |
| WO | WO 99/30622 A2 | 6/1999 |
| WO | WO 02/11621 A1 | 2/2002 |
| WO | WO 02/34122 A2 | 5/2002 |
| WO | WO 02/094082 A2 | 11/2002 |
| WO | WO 03/045260 A1 | 6/2003 |
| WO | WO 03/078721 A2 | 9/2003 |
| WO | WO 2004/086984 A1 | 10/2004 |
| WO | WO 2005/009211 A2 | 2/2005 |
| WO | WO 2005/018467 A2 | 3/2005 |
| WO | WO 2005/065284 A2 | 7/2005 |
| WO | WO 2005/112810 A2 | 12/2005 |
| WO | WO 2005/120363 A1 | 12/2005 |
| WO | WO 2006/007399 A1 | 1/2006 |
| WO | WO 2006/041881 A2 | 4/2006 |
| WO | WO 2006/060405 A2 | 6/2006 |
| WO | WO 2006/113216 A2 | 10/2006 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2008/076800 A2 | 6/2008 |
| WO | WO 2009/027065 A1 | 3/2009 |

OTHER PUBLICATIONS

K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).

K. Sumiyama et al., "Submucosal Endoscopy with Mucosal Flap Safety Valve," Gastrointest Endosc. Apr. 2007, vol. 65(4) pp. 694-695 (Abstract).

K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).

K. Sumiyama et al., "Endoscopic Caps," Tech. Gastrointest. Endosc., vol. 8, pp. 28-32, 2006.

"Z-Offset Technique Used in the Introduction of Trocar During Laparoscopic Surgery," M.S. Hershey NOTES Presentation to EES NOTES Development Team, Sep. 27, 2007.

F.N. Denans, Nouveau Procede Pour La Guerison Des Plaies Des Intestines. Extrait Des Seances De La Societe Royale De Medecine De Marseille, Pendant Le Mois De Decembre 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).

I. Fraser, "An Historical Perspective on Mechanical Aids in Intestinal Anastamosis," Surg. Gynecol. Obstet. (Oct. 1982), vol. 155, pp. 566-574.

M.E. Ryan et al., "Endoscopic Intervention for Biliary Leaks After Laparoscopic Cholecystectomy: A Multicenter Review," Gastrointest. Endosc., vol. 47(3), 1998, pp. 261-266.

C. Cope, "Creation of Compression Gastroenterostomy by Means of the Oral, Percutaneous, or Surgical Introduction of Magnets: Feasibility Study in Swine," J. Vasc Intery Radiol, (1995), vol. 6(4), pp. 539-545.

J.W. Hazey et al., "Natural Orifice Transgastric Endoscopic Peritoneoscopy in Humans: Initial Clinical Trial," Surg Endosc, (Jan. 2008), vol. 22(1), pp. 16-20.

N. Chopita et al., "Endoscopic Gastroenteric Anastamosis Using Magnets," Endoscopy, (2005), vol. 37(4), pp. 313-317.

C. Cope et al., "Long Term Patency of Experimental Magnetic Compression Gastroenteric Anastomoses Achieved with Covered Stents," Gastrointest Endosc, (2001), vol. 53, pp. 780-784.

H. Okajima et al., "Magnet Compression Anastamosis for Bile Duct Stenosis After Duct to Duct Biliary Reconstruction in Living Donor Liver Transplantation," Liver Transplantation (2005), pp. 473-475.

A. Fritscher-Ravens et al., "Transluminal Endosurgery: Single Lumen Access Anastamotic Device for Flexible Endoscopy," Gastrointestinal Endosc, (2003), vol. 58(4), pp. 585-591.

G.A. Hallenbeck, M.D. et al., "An Instrument for Colorectal Anastomosis Without Sutrues," Dis Col. Rectum, (1963), vol. 5, pp. 98-101.

T. Hardy, Jr., M.D. et al., "A Biofragmentable Ring for Sutureless Bowel Anastomosis. An Experimental Study," Dis Col. Rectum, (1985), vol. 28, pp. 484-490.

P. O'Neill, M.D. et al., "Nonsuture Intestinal Anastomosis," Am J. Surg, (1962), vol. 104, pp. 761-767.

C.P. Swain, M.D. et al., "Anastomosis at Flexible Endoscopy: An Experimental Study of Compression Button Gastrojejunostomy," Gastrointest Endosc, (1991), vol. 37, pp. 628-632.

J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.

USGI® EndoSurgical Operating System—g-Prox® Tissue Grasper/Approximation Device; [online] URL: http://www.usgimedical.com/eos/components-gprox.htm—accessed May 30, 2008 (2 pages).

Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.

Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).

ERCP; Jackson Siegelbaum Gastroenterology; [online] URL: http://www.gicare.com/pated/epdgs20.htm; accessed Feb. 21, 2008 (3 pages).

D.G. Fong et al., "Transcolonic Ventral Wall Hernia Mesh Fixation in a Porcine Model," Endoscopy 2007; 39: 865-869.

B. Rubinsky, Ph.D., "Irreversible Electroporation in Medicine," Technology in Cancer Research and Treatment, vol. 6, No. 4, Aug. 2007, pp. 255-259.

D.B. Nelson, MD et al., "Endoscopic Hemostatic Devices," Gastrointestinal Endoscopy, vol. 54, No. 6, 2001, pp. 833-840.

CRE™ Pulmonary Balloon Dilator; [online] URL: http://www.bostonscientific.com/Device.bsci?page=HCP_Overview &navRelId=1000.1003&method=D..., accessed Jul. 18, 2008 (4 pages).

U.S. Appl. No. 11/894,358, filed Aug. 21, 2007.
U.S. Appl. No. 11/897,676, filed Aug. 31, 2007.
U.S. Appl. No. 11/968,810, filed Jan. 3, 2008.
U.S. Appl. No. 11/981,070, filed Oct. 31, 2007.
U.S. Appl. No. 11/981,078, filed Oct. 31, 2007.
U.S. Appl. No. 11/981,134, filed Oct. 31, 2007.
U.S. Appl. No. 11/986,084, filed Nov. 20, 2007.
U.S. Appl. No. 11/986,420, filed Nov. 21, 2007.
U.S. Appl. No. 11/986,489 filed Nov. 21, 2007.
U.S. Appl. No. 11/998,370, filed Nov. 29, 2007.
U.S. Appl. No. 12/014,417, filed Jan. 5, 2008.
U.S. Appl. No. 12/019,461, filed Jan. 24, 2008.
U.S. Appl. No. 12/045,318, filed Mar. 10, 2008.
U.S. Appl. No. 12/109,673, filed Apr. 25, 2008.
U.S. Appl. No. 12/109,699, filed Apr. 25, 2008.
U.S. Appl. No. 12/115,916, filed May 6, 2008.
U.S. Appl. No. 12/122,031, filed May 16, 2008.
U.S. Appl. No. 12/129,784, filed May 30, 2008.
U.S. Appl. No. 12/129,880, filed May 30, 2008.
U.S. Appl. No. 12/130,010, filed May 30, 2008.
U.S. Appl. No. 12/130,023, filed May 30, 2008.
U.S. Appl. No. 12/130,224, filed May 30, 2008.
U.S. Appl. No. 12/130,652, filed May 30, 2008.
U.S. Appl. No. 12/133,109, filed Jun. 4, 2008.
U.S. Appl. No. 12/133,953, filed Jun. 5, 2008.
U.S. Appl. No. 12/163,255, filed Jun. 27, 2008.
U.S. Appl. No. 12/169,868, filed Jul. 9, 2008.
U.S. Appl. No. 12/170,862, filed Jul. 10, 2008.
U.S. Appl. No. 12/172,752, filed Jul. 14, 2008.
U.S. Appl. No. 12/172,766, filed Jul. 14, 2008.

U.S. Appl. No. 12/172,782, filed Jul. 14, 2008.
U.S. Appl. No. 12/192,372, filed Aug. 15, 2008.
U.S. Appl. No. 12/203,330, filed Sep. 3, 2008.
U.S. Appl. No. 12/197,749, filed Aug. 25, 2008.
U.S. Appl. No. 12/197,653, filed Aug. 25, 2008.
U.S. Appl. No. 12/202,740, filed Sep. 2, 2008.
U.S. Appl. No. 12/203,458, filed Sep. 3, 2008.
U.S. Appl. No. 12/201,812, filed Aug. 29, 2008.
U.S. Appl. No. 12/207,306, filed Sep. 9, 2008.
U.S. Appl. No. 12/243,334, filed Oct. 1, 2008.
U.S. Appl. No. 12/234,425, filed Sep. 19, 2008.
U.S. Appl. No. 12/060,601, filed Apr. 1, 2008.
U.S. Appl. No. 11/952,475, filed Dec. 7, 2007.
U.S. Appl. No. 12/277,975, filed Nov. 25, 2008.
U.S. Appl. No. 12/277,957, filed Nov. 25, 2008.
U.S. Appl. No. 12/332,938, filed Dec. 11, 2008.
U.S. Appl. No. 12/337,340, filed Dec. 17, 2008.
U.S. Appl. No. 12/352,451, filed Jan. 12, 2009.
U.S. Appl. No. 12/359,824, filed Jan. 26, 2009.
U.S. Appl. No. 12/352,375, filed Jan. 12, 2009.
U.S. Appl. No. 12/359,053, filed Jan. 23, 2009.
U.S. Appl. No. 12/362,826, filed Jan. 30, 2009.
U.S. Appl. No. 12/363,137, filed Jan. 30, 2009.
U.S. Appl. No. 12/364,172, filed Feb. 2, 2009.
U.S. Appl. No. 12/364,256, filed Feb. 2, 2009.
Fritscher-Ravens, et al., "Transgastric Gastropexy and Hiatal Hernia Repair for GERD Under EUS Control: a Porcine Model," American Society for Gastrointestinal Endoscopy, Mar. 14, 2003.
Michael S. Kavic, M.D., "Natural Orifice Translumenal Endoscopic Surgery: "NOTES"", JSLS, vol. 10, pp. 133-134 (2006).
Ethicon, Inc., "Wound Closure Manual: Chapter 3 (The Surgical Needle)," pp. 41-54 (publication date unknown).
Guido M. Scalabas, M.D., et al., "Endoluminal methods for Gastrotomy Closure in Natural Orifice TransEnteric Surgery (NOTES)," Surgical Innovation, vol. 13(1), pp. 23-30, Mar. 2006.
Ogando, "Prototype Tools That Go With The Flow," Design News, Jul. 17, 2006.
Edd, et al., "In Vivo Results of a New Focal Tissue Ablation Technique: Irreversible Electroporation," IEEE Trans Biomed Eng, vol. 53, pp. 1409-1415, 2006.
Kennedy, et al., "High-Burst-Strength, Feedback-Controlled Bipolar Vessel Sealing," Surgical Endoscopy, vol. 12, pp. 876-878 (1998).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).
J.D. Paulson, M.D., et al., "Development of Flexible Culdoscopy," The Journal of the American Association of Gynecologic Laparoscopists, Nov. 1999, vol. 6, No. 4, pp. 487-490.
H. Seifert, et al., "Retroperitoneal Endoscopic Debridement for Infected Peripancreatic Necrosis," The Lancet, Research Letters, vol. 356, Aug. 19, 2000, pp. 653-655.
K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Received Oct. 3, 1997; Accepted Mar. 31, 1998).
U.S. Appl. No. 12/413,479, filed Mar. 27, 2009.
U.S. Appl. No. 12/468,462, filed May 19, 2009.
D. Wilhelm et al., "An Innovative, Safe and Sterile Sigmoid Access (ISSA) for NOTES," Endoscopy 2007, vol. 39, pp. 401-406.
Nakazawa et al., "Radiofrequency Ablation of Hepatocellular Carcinoma: Correlation Between Local Tumor Progression After Ablation and Ablative Margin," AJR, 188, pp. 480-488 (Feb. 2007).
Miklavčič et al., "A validated model of in vivo electric field distribution in tissues for electrochemotherapy and for DNA electrotransfer for gene therapy," Biochimica et Biophysica Acta, 1523, pp. 73-83 (2000).
Evans, "Ablative and cathether-delivered therapies for colorectal liver metastases (CRLM)," EJSO, 33, pp. S64-S75 (2007).
Wong et al., "Combined Percutaneous Radiofrequency Ablation and Ethanol Injection for Hepatocellular Carcinoma in High-Risk Locations," AJR, 190, pp. W187-W195 (2008).
Heller et al., "Electrically mediated plasmid DNA delivery to hepatocellular carcinomas in vivo," Gene Therapy, 7, pp. 826-829 (2000).
Widera et al., "Increased DNA Vaccine Delivery and Immunogenicity by Electroporation In Vivo," The Journal of Immunology, 164, pp. 4635-4640 (2000).
Weaver et al., "Theory of electroporation: A review," Bioelectrochemistry and Bioenergetics, 41, pp. 135-160 (1996).
Mulier et al., "Radiofrequency Ablation Versus Resection for Resectable Colorectal Liver Metastases: Time for a Randomized Trial?" Annals of Surgical Oncology, 15(1), pp. 144-157 (2008).
Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).
Guyton et al., "Membrane Potentials and Action Potentials," W.B. Sanders, ed. Textbook of Medical Physiology, p. 56 (2000).
Guyton et al., "Contraction of Skeletal Muscle," Textbook of Medical Physiology, pp. 82-84 (2000).
"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).
"Ethicon Endo-Surgery Studies Presented At DDW Demonstrate Potential Of Pure NOTES Surgery With Company's Toolbox," Jun. 3, 2009 Press Release; URL http://www.jnj.com/connect/news/product/20090603_120000; accessed Aug. 28, 2009 (3 pages).
Castellvi et al., "Hybrid Transvaginal NOTES Sleeve Gastrectomy in a Porcine Model Using A Magnetically Anchored Camera and Novel Instrumentation," Abstract submitted along with Poster at SAGES Annual Meeting in Phoenix, AZ, Apr. 22, 2009 (1 page).
Castellvi et al., "Hybrid Transvaginal NOTES Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).

* cited by examiner

SURGICAL SUTURE ANCHORS AND DEPLOYMENT DEVICE

FIELD OF THE INVENTION

The invention relates to surgical suture anchors and a tool for deploying them, and more particularly to suture anchors that can be deployed to anchor sutures already in place in tissue.

BACKGROUND

Sutures are used to approximate, or bring together, tissue separated, for example, by some trauma, or wound or during a surgical procedure to close an incision or an organ perforation. Suturing instruments generally include a needle and a trailing length of suture material. In endoscopic procedures, the instruments placed through an instrument channel may include needles and sutures for stitching such a wound, incision or perforation within the patient's body cavity. An exemplary suturing device is shown in U.S. Pat. No. 7,131,978.

In some cases, the leading, or distal end, of the suture material is attached during manufacture to a small anchor, sometimes referred to as a T-tag, to stabilize the tissue and the suture as the surgeon pulls the suture material through tissue. Anchors are commonly utilized to retain sutures in a patient's body. The anchors may be formed of metal, such as stainless steel or titanium, or of a biodegradable material. Several known anchors rely upon mechanical interlocks between the body tissue and the anchor to retain the anchor in place against the influence of forces transmitted through the suture to the anchor. It has previously been suggested to construct anchors in the manner disclosed in U.S. Pat. Nos. 5,405,359; 5,403,348; 5,203,787; 5,046,513; and 5,041,129.

In many cases, however, the suture does not include an anchor and the ends of the suture are tied using conventional suturing and knotting techniques. Only after the wound or incision is sutured, does the practitioner, such as a surgeon, physician, or clinician, determine that a suture anchor is needed. It is not believed that securing sutures with an anchor, after the suture is already in place, has heretofore been done. It is the current thought that the wound or incision would have to be sutured a second time with an anchor/suture combination.

Physicians have often used endoscopes to examine, to biopsy, and to ablate the tissue of patients within lumens such as the esophageous and the bowel or other body cavity and internal patient sites. An endoscope generally includes either a rigid or flexible tube containing one or more optical fiber systems and, for operative uses (human or veterinary), one or more channels for passage of medical instruments. The optical system includes a light delivery system to illuminate the organ or site under inspection and a camera system to transmit the image of the site of interest to the viewer. The light source is normally outside the body and the light is typically directed via optical fiber bundles to the area of interest. A physician performing a therapeutic procedure with the use of an endoscope places a long, flexible instrument through the endoscope's instrument channel and then positions the instrument near the site within the body cavity, lumen or other internal site of interest where a therapeutic procedure is to be performed.

SUMMARY OF THE INVENTION

A suture anchor for securing a section of a suture already in place in a patient's tissue is provided. The suture anchor includes a hollow member having an outer surface defining an enclosure, the hollow member having a longitudinal axis and a slot through a portion of the outer surface in a direction transverse to the longitudinal axis, the slot providing an opening into the enclosure. The suture anchor further includes a one-way valve positioned within the enclosure at the slot to allow entry of a suture through the opening into the enclosure and to prevent the exit of the suture from the enclosure. In one embodiment, the one-way valve is a leaf spring biased toward contact with a surface of the enclosure and positioned such that it spans at least a portion of the opening in a direction parallel to the longitudinal axis of the hollow member.

The slot may be configured such that it forms a straight cut through the hollow member at an angle relative to the longitudinal axis of the hollow member. The cut is preferably configured such that it defines an apex and a pair of end sections. When the hollow member is a cylinder, the cut will appear as an ellipse. However, the hollow member may form a number of different shapes and is not limited to a cylinder.

In another embodiment, the one-way valve may be a resilient wire having a first end attached to a first surface of the enclosure and a second free end biased toward contact with a second surface of the enclosure, wherein the second surface of the enclosure faces and is spaced from the first surface of the enclosure. The second free end in this embodiment is positioned such that it spans the cut of the slot at the apex thereof in a direction parallel to the longitudinal axis of the hollow member.

A device is provided for deploying the suture anchor. The deployment device includes an elongate hollow member having a longitudinal axis, a distal end and a proximal end, a tip of reduced diameter relative to the elongate member at the distal end of the elongate member, a suture anchor release zone in the elongate member positioned adjacent to and proximal to the tip, a launch bar having at least a portion thereof positioned in the release zone, wherein the launch bar is movable within the release zone between a resting position and a launching position and is operatively connected to an actuation member positioned at the proximal end of the elongate member. The hollow elongate member defines a housing for receiving a plurality of suture anchors in tandem along the longitudinal axis of the hollow member, wherein each of the suture anchors is configured for release from the release zone when positioned within the release zone upon movement of the launch bar from the resting position to the launching position.

The release zone is shown in one embodiment herein as configured for holding a single suture anchor therein until the launch bar is moved to the launching position.

In the embodiment shown herein suitable for use with an endoscope, the elongate member is a cylinder dimensioned in cross-section to allow the elongate member to pass through a channel leading to an internal site in a patient. The tip is preferably conical in shape. The release zone is shown in one embodiment to define an opening in the elongate member.

A method for deploying one or more suture anchors is also provided. Further, a method for sterilizing and packaging the deployment device is also provided.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION

Figure 1:
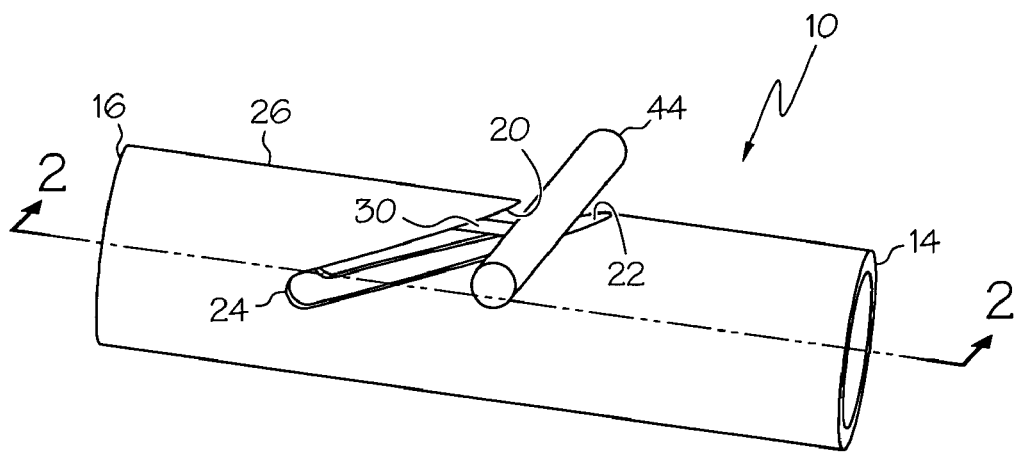
FIG. 1 is a perspective view of a surgical suture anchor and a section of a suture.

Before the present method and embodiments of an instrument are disclosed and described, it is to be understood that this invention is not limited to the particular process steps and materials disclosed herein as such process steps and materials may vary somewhat. It is also to be understood that the terminology used herein is used for the purpose of describing particular embodiments only and is not intended to be limiting since the scope of the present invention will be limited only by the appended claims.

Unless defined otherwise, all technical and scientific terms used herein have the same meaning as commonly understood to one of ordinary skill in the art to which this invention belongs. Although any method, instrument and materials similar or equivalent to those described herein may be used in the practice or testing of the invention, particular embodiments of a method, instrument and materials are now described.

It must be noted that, as used in this specification and the appended claims, the singular forms "a," "an," and "the" include plural referents unless the content clearly dictates otherwise.

In describing and claiming the present invention, the following terminology will be used in accordance with the definitions set out below.

As used herein, the term "patient," used herein, refers to any human or animal on which a suturing procedure may be performed.

As used herein, the term "biocompatible" includes any material that is compatible with the living tissues and system(s) of a patient by not being substantially toxic or injurious and not causing immunological rejection. "Biocompatibility" includes the tendency of a material to be biocompatible.

As used herein, the term "bioabsorbable" includes the ability of a material to be dissolved and/or degraded, and absorbed, by the body.

As used herein, the term "proximal" (or any form thereof), with respect to a component of an instrument, means that portion of the component that is generally nearest the practitioner, physician, or surgeon, or nearest to the end of the instrument handled by the practitioner, physician, or surgeon, when in use; and with respect to a direction of travel of a component of an instrument, means toward the end of the instrument generally nearest the practitioner, physician, or surgeon, or handled by the practitioner, physician, or surgeon, when in use.

As used herein, the term "distal" (or any form thereof), with respect to a component of an instrument, means that portion of the component that is generally farthest from the practitioner, physician, or surgeon, or farthest from the end of the instrument handled by the practitioner, physician, or surgeon, when in use; and with respect to a direction of travel of a component of an instrument, means away from the end of the instrument generally nearest the practitioner, physician, or surgeon, or handled by the practitioner, physician, or surgeon, when in use.

As used herein, the term "transverse" (or any form thereof), with respect to an axis, means extending in a line, plane or direction that is across such axis, i.e., not collinear or parallel therewith. "Transverse" as used herein is not to be limited to "perpendicular As used herein, the term "longitudinal axis", with respect to an instrument, means the exact or approximate central axis defined by said instrument along its greater dimension, i.e., along its length, from its distal end to its proximal end, and vice versa, and is not intended to be limited to imply a straight line, wherein, for example, an instrument includes a bend angle as described herein, it is intended that "longitudinal axis" as used herein follows such bend angle.

As used herein, the term "internal site" of a patient means a lumen, body cavity or other location in a patient's body including, without limitation, sites accessible through natural orifices or through incisions.

The present invention has application in conventional endoscopic and open surgical instrumentation, as well as application in robotic-assisted surgery. The embodiments shown illustrate the use of the invention in connection with an endoscope within an internal site of a patient. The invention is useful in a variety of minimally invasive medical procedures, including without limitation medical procedures performed through laparoscopic incisions for access to body cavities and internal organs of the body. The invention also encompasses apparatus and methods employing endoscopic devices in general, including various forms and variations of endoscopes, including without limitation: laparoscopes, gastroscopes, peritoneoscopes, sigmoidoscopes, fiberoptic endoscopes, arthroscopes, amnioscopes, and the like.

Referring to FIGS. 1-4, the embodiment of the suture anchor 10 includes a hollow cylinder 26 which may be open or closed at one or both ends 14, 16 and defines an internal chamber or lumen 12. A slot 20 is cut into the cylinder 26, in a direction transverse to the longitudinal axis 18 of cylinder 26, beginning at an apex 22 and ending at bottom ends 24. To facilitate the smooth entry of a section of suture 44, the slot 20 is preferably cut at an acute or obtuse angle relative to the axis 18, rather than cut perpendicular to the axis 18. In one embodiment, the slot is configured such that it forms a cut through the hollow cylinder 26 at an angle relative to the longitudinal axis 18 of the cylinder 26. The cut of the slot defines an apex 22 and a pair of end sections 24.

Figure 2:
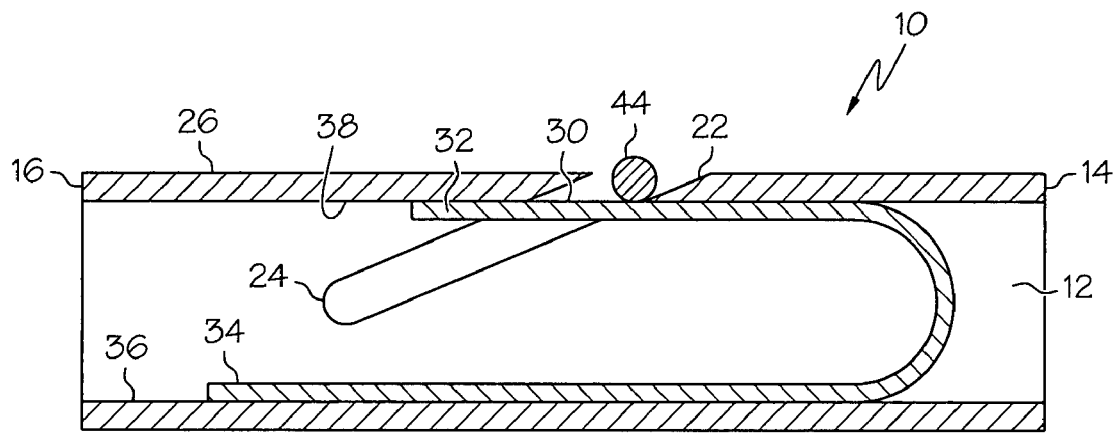
FIG. 2 is a section view through the line 2-2 of FIG. 1, showing the suture at the entry of the slot but still outside of the suture anchor.
Figure 3:
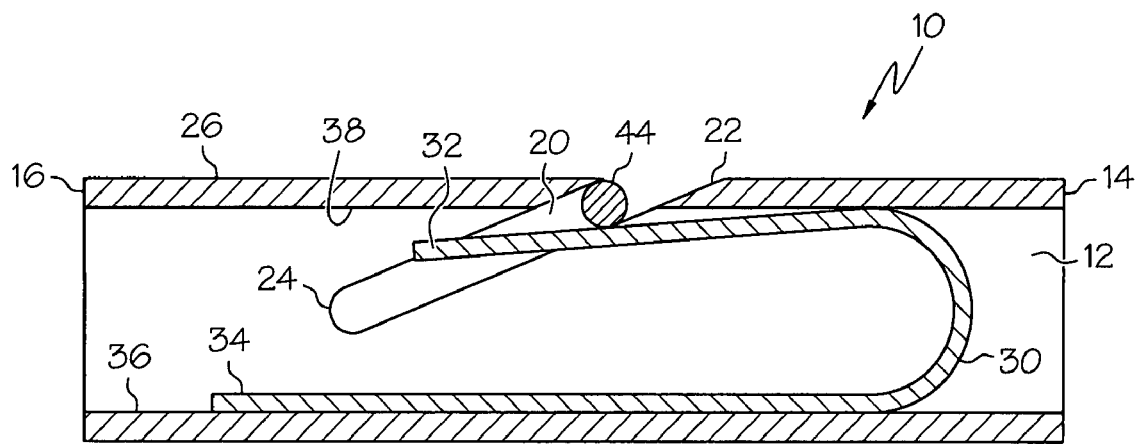
FIG. 3 is a section view through the line 2-2 of FIG. 1 showing the suture entering the slot in the suture anchor.

A valve 30 is housed in the lumen 12 of anchor 10. In the embodiment shown, the valve may be a leaf spring, formed from a flexible, but resilient wire or band attached at one end 34 to a bottom surface 36 of lumen 12. A free end 32 of valve 30 is biased toward the top surface 38 of lumen 12, forming a one way gate at slot 20 into lumen 12. The leaf spring wire or band bends over itself as shown in FIGS. 2-3 to create the spring-like tension in valve 30.

Figure 11:
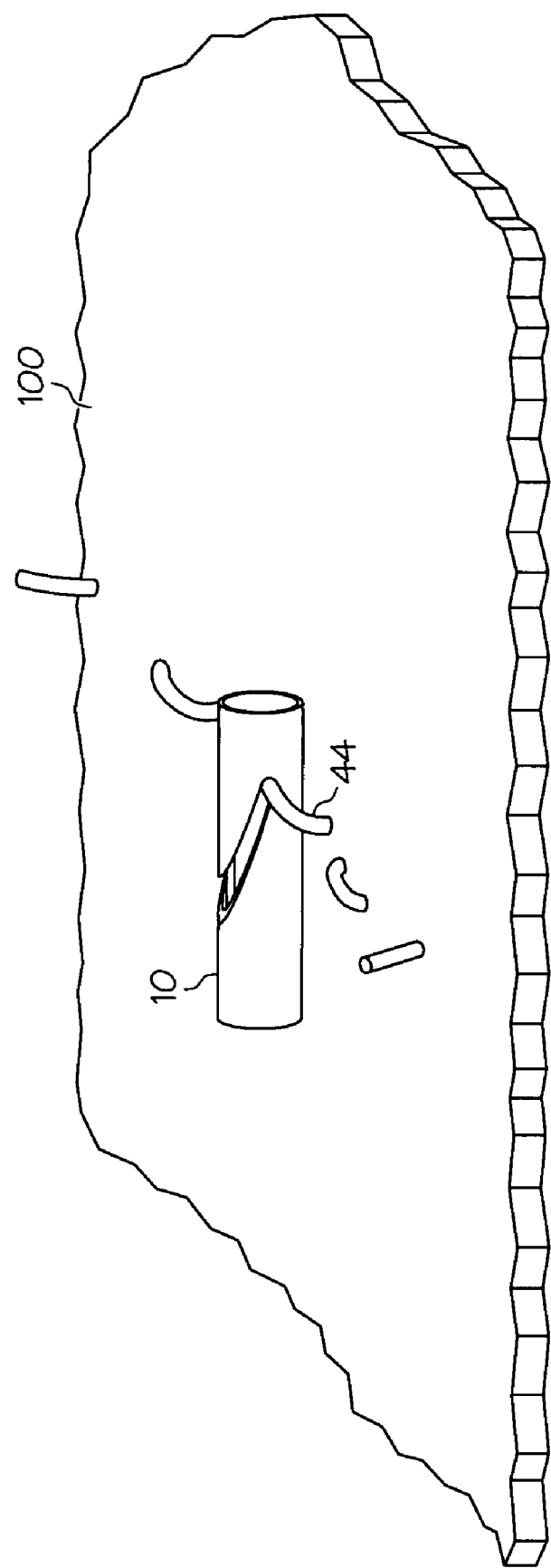
FIG. 11 is a view of a suture anchor engaging a section of suture in tissue following the completion of the anchor deployment procedure.

In use, the anchor 10 would be advanced toward a section of suture 44 stitched into tissue 100. The anchor 10 would be advanced distally. The anchor 10 is passed under the suture 44 with the side of cylinder 26 having the apex 22 of slot 20 facing the suture 44, away from the tissue 100. The suture 44 slides into the open apex end 22 of slot 20, as shown in FIG. 2. As the anchor 10 is advanced against the suture section 44, suture 44 presses against the free end 32 of valve 30 as shown in FIG. 3, pushing it downward into lumen 12 enough to allow suture 44 to slide down slot 20, past the free end 32 of valve 30, to rest at bottom ends 24 of slot 20. When anchor 10 is advanced to the point where suture 44 is past free end 32, free end 32 snaps back to its original position against top surface 38 of lumen 12, closing the "gate" at slot 20 and thereby preventing suture 44 from exiting the slot 20. Anchor 10 is thus attached to the suture 44 between the suture 44 and the tissue 100 to assist in securing the suture 44 to the tissues 100, as shown in FIG. 11.

Figure 5:
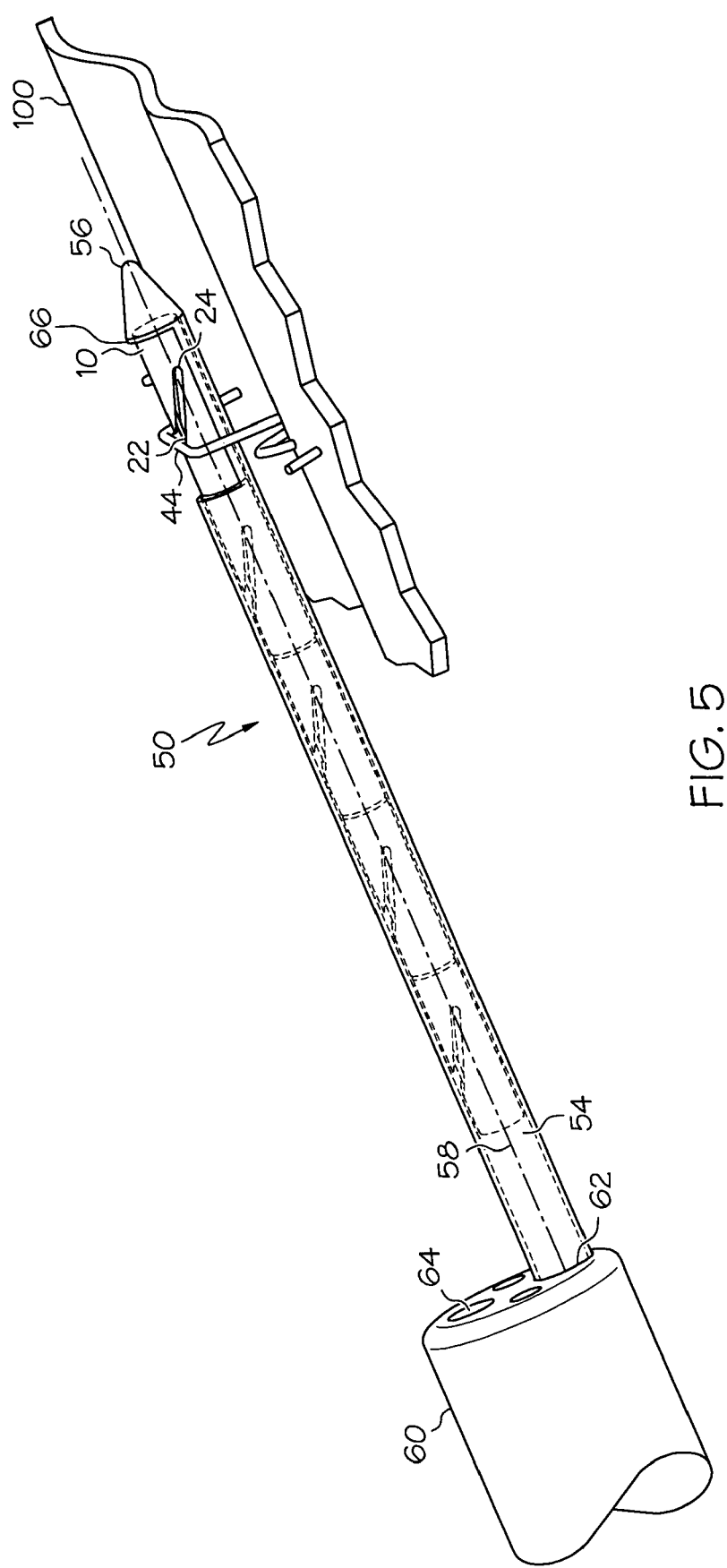
FIG. 5 is a perspective view of a suture anchor being deployed to a section of suture.

Referring to FIGS. 5-10, an embodiment of a suture anchor deployment device 50 is shown. In FIG. 5, the deployment device 50 is shown extending from a working channel 62 of an endoscope 60. The deployment device 50 may be used with any suitable known endoscope having at the distal end thereof, a camera and lights 64 to enable the practitioner to see the internal site of the patient, and one or more working channels 62 through which various instruments are typically inserted to allow the practitioner to perform desired procedures at the internal site. The working channel 62 includes a longitudinal axis (not shown), as defined herein.

In one embodiment, deployment device 50 includes a hollow cylinder or tube 52 with an open lumen 54 defining a housing in which a plurality of anchors 10 may be positioned in tandem for deployment to anchor in-place sections of suture 44. Deployment cylinder 52 has a longitudinal axis 58. The anchors 10 line up such that the longitudinal axes 18 of the anchors 10 are co-linear to, or parallel to, the longitudinal axis 58 of the deployment cylinder 52. In the orientation shown in FIGS. 5-10, end 16 of anchor 10 is positioned distally and end 14 is proximal to the suture 44 to be anchored. Those skilled in the art will recognize that the orientation of the anchors 10 may change such that end 14 is positioned distally and end 16 is proximal to the suture 44 to be anchored. The difference in orientation would require different maneuvering from the practitioner to secure the anchor 10 to suture section 44.

At the distal end 70 of cylinder 52 is a cone-shaped tip 56 of reduced diameter relative to the cross-sectional dimension of the elongate member. The tip 56 facilitates passage of the distal end 70 of deployment device 50 under suture section 44. Just behind tip 56 is an opening 72 in cylinder 52 which functions as a release zone for the suture anchors. The opening 72 is about the same length as the length of an anchor 10. The length of opening 72 may be less that the length of cylinder 52 so that the proximal end 16 of anchor 10 is in sufficient contact with cylinder 52 to hold the leading anchor 10 in place until the desired section of suture 44 is captured in slot 20. The overlap between the end 16 of anchor 10 and the cylinder 52 should not, however, interfere with the launch of anchor 10 from the opening 72 at the release zone.

Figure 6:
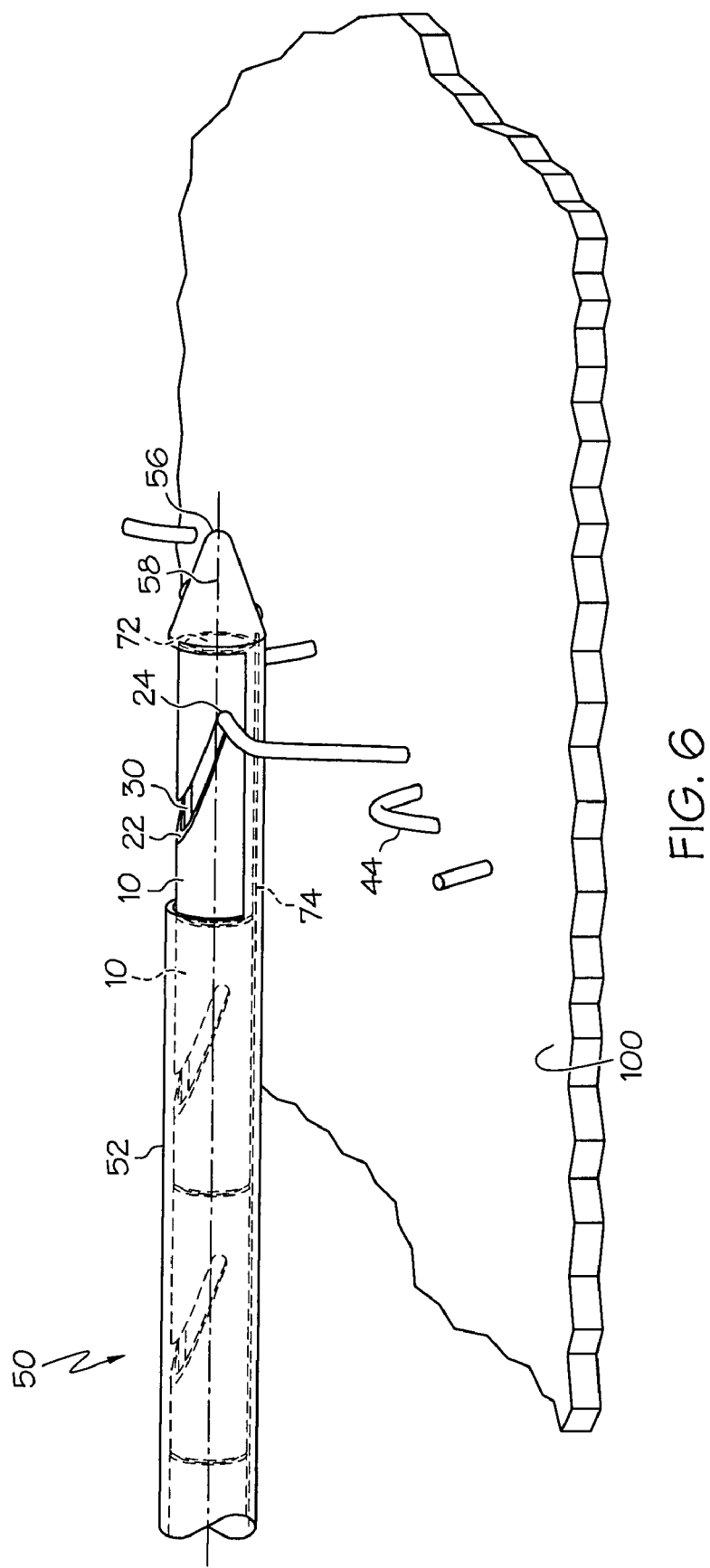
FIG. 6 is a view of a suture anchor in the deployment device showing the suture captured in the anchor, as in FIG. 4.

A launch bar 74, as shown in a launching configuration in FIGS. 7-10, runs along the bottom interior surface 80 of the lumen 54 of cylinder 52. The launch bar 74 has a resting position as shown in FIGS. 5 and 6 wherein the launch bar 74 is flat. When the anchor 10 is to be released from deployment device 50, as may be determined by the practitioner based on the image observed due to the optical system and camera 64 communicated through the endoscope, the practitioner moves launch bar 74 from its resting position to its launching position by causing the launch bar 74 to be pushed forward (by actuation, for example, of a push rod or a control operatively connected to a push rod, not shown, which applies a force in the distal direction against the proximal end of launch bar 74), in a distal direction, along cylinder bottom 80. The force in the distal direction causes launch bar 74 to bend at first and second joints 76, 78. The section of launch bar 74 between joint 76 and the distal end of launch bar 74 pops up, with joint 78 forming the apex of a triangle, and thus assuming the launching position.

The anchors 10 may be made of stainless steel, titanium, nitonal (a nickel-titanium shape memory alloy) or any biocompatible material or bioabsorbable material. As used herein, "shape memory" refers to the tendency of a material to return to a preformed shape following deformation.

Deployment device 50 may be made of any suitable biocompatible material. Deployment device 50, and in particular, cylinder 52 thereof is preferably made of a flexible material to allow deployment device 50 to travel through the length of the working channel 62 of an endoscope 60, which in many embodiments, will require flexibility to enter a patient's internal sites, particularly if inserted through a natural orifice. In recent literature, a procedure is advanced in which an endoscope is passed through a natural orifice (mouth, anus, etc.), then through an internal incision in the stomach or colon, for example, to avoid any external incisions or scars.

Referring to the sequence shown in FIGS. 5-11, deployment device 50 is advanced distally through a working channel 62 of endoscope 60. In the orientation shown, an anchor 10 is positioned in the release zone, at opening 72 of the cylinder 52 of deployment device 50 with slot 20 exposed to the suture 44. Tip 56 of deployment device 50 is eased under a section of suture 44. The suture 44 slides up the cone shaped tip 56, onto the exposed surface of anchor 10. Deployment device 50 is advanced to position the apex 22 of slot 20 of anchor 10 under suture 44.

Figure 4:
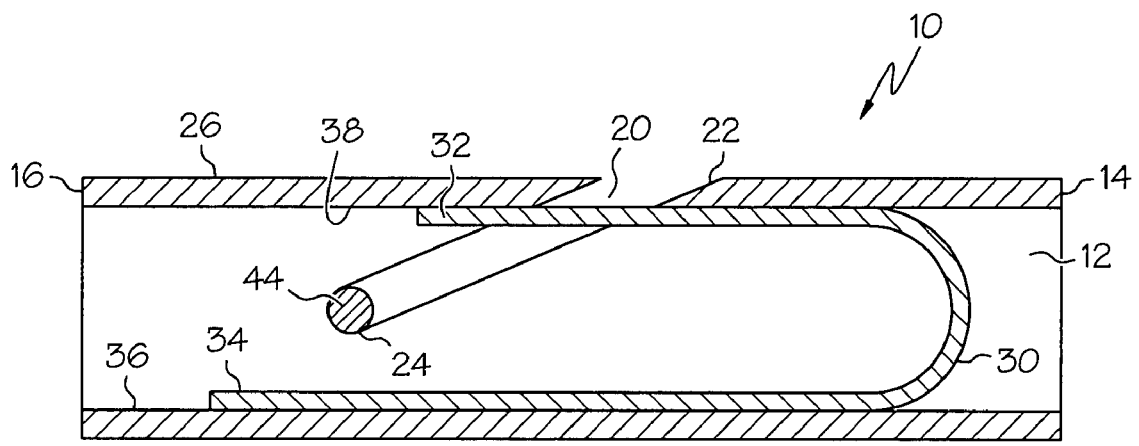
FIG. 4 is a section view through the line 2-2 of FIG. 1 showing the suture captured in the suture anchor.

Referring to FIG. 6, the deployment device 50 is pulled back in a proximal direction to slide suture section 44 down slot 20 of anchor 10, past valve 30 as shown in FIGS. 3 and 4. Valve 30 snaps back into the closed position, thereby securely attaching anchor 10 to suture section 44.

Figure 7:
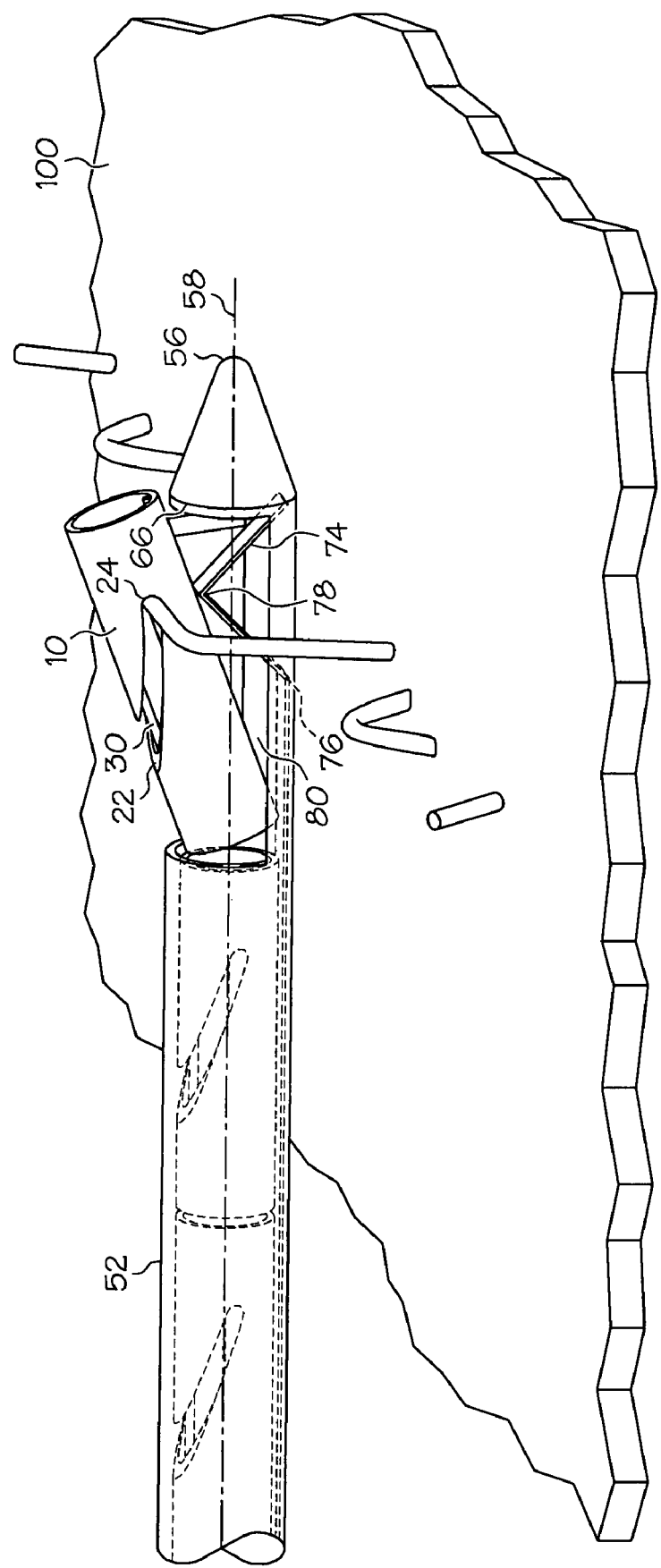
FIG. 7 is a view of the suture anchor being ejected from the deployment device.
Figure 8:
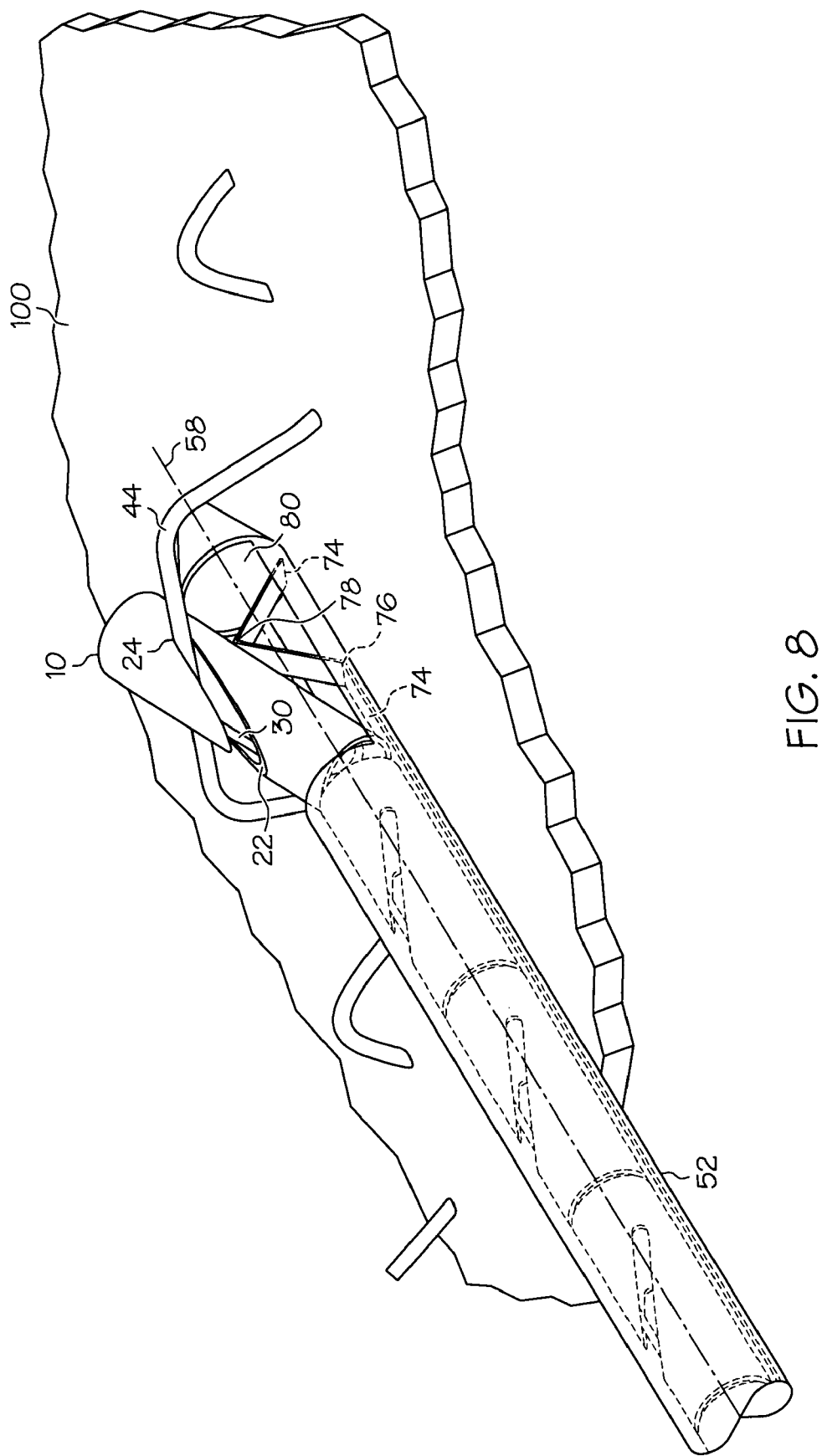
FIG. 8 is an alternative view of the ejection of the suture anchor of FIG. 7.
Figure 9:
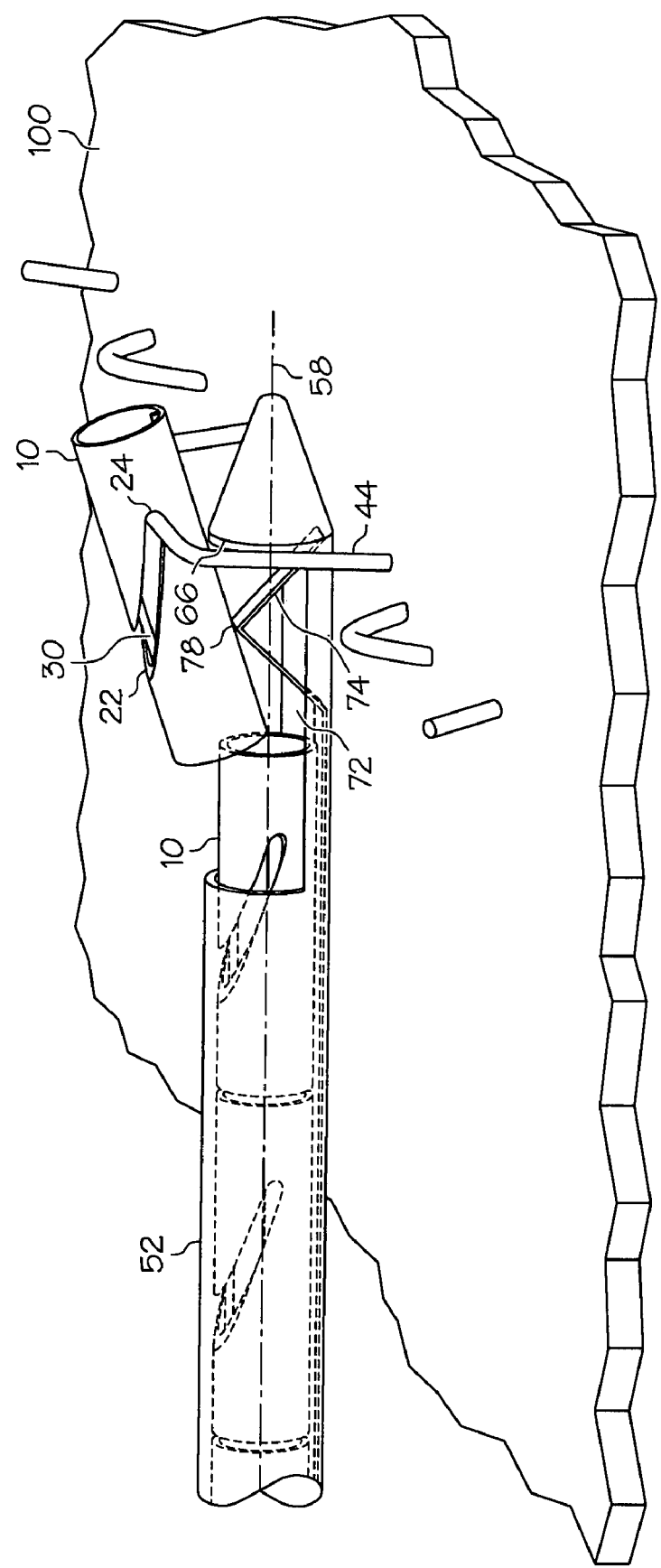
FIG. 9 is a view of the deployment device being withdrawn from the suture and deployed anchor.
Figure 10:
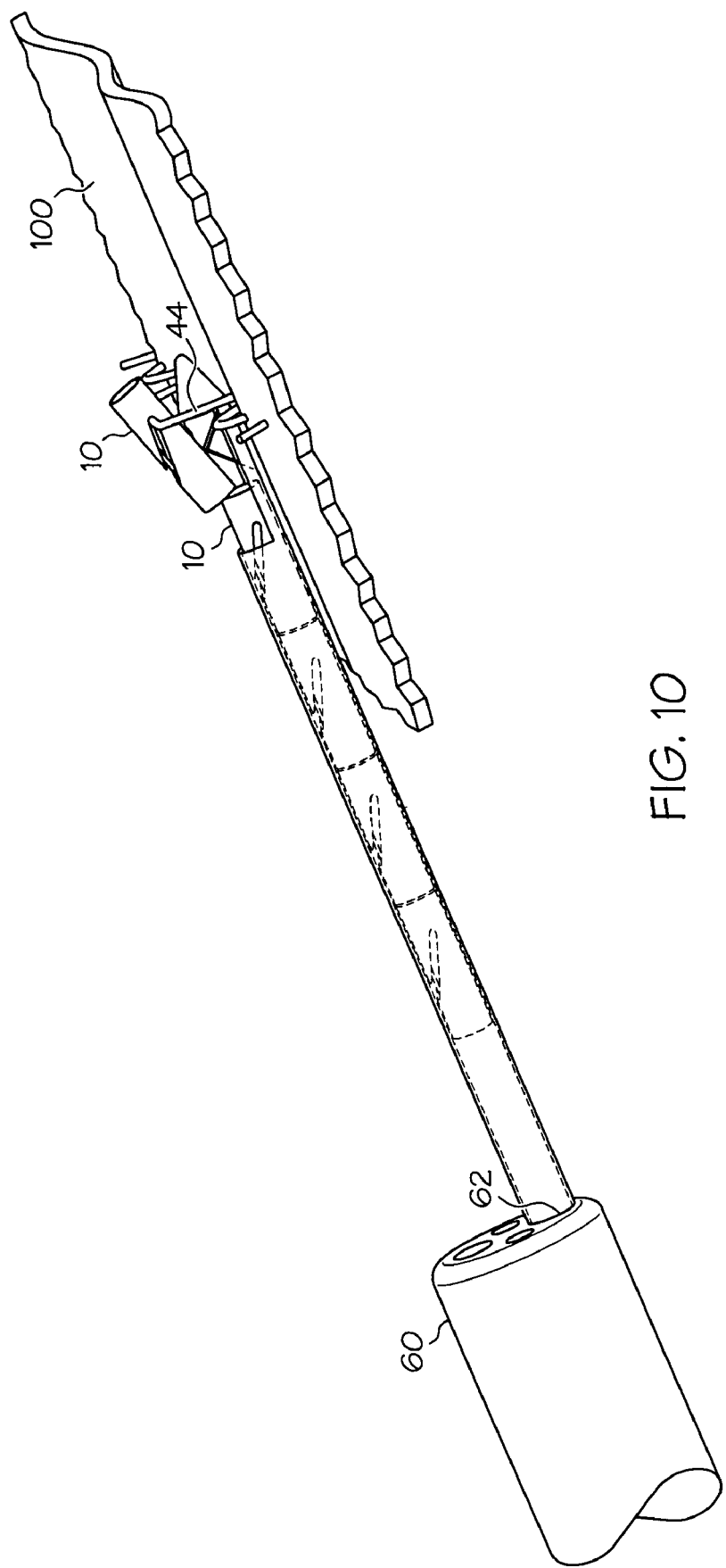
FIG. 10 is a view of the deployment device of FIG. 9 being drawn back into the endoscope.

To release anchor 10, launch bar 74 is moved from the flat resting position shown in FIG. 6 to the launching position shown in FIGS. 7 and 8. The apex formed by joint 78 of launch bar 74 pushes the distal end 16 of anchor 10 upwardly, out of release zone opening 72. Deployment device 50 is pulled back in the proximal direction into the endoscope 60, moving the rim 66 of tip 56 along the bottom of anchor 10 while the apex 78 of launch bar 74 lifts the proximal end 14 of anchor 10 upwardly and out of the opening 72 at the release zone of cylinder 52.

When the deployment device 50 is completely withdrawn from beneath suture section 44, anchor 10 remains to anchor the suture 44 in position, as shown in FIG. 11, inhibiting the suture 44 from migrating through tissue 100.

As the leading anchor 10 is released or launched from the deployment device 50, the next anchor 10 in line within cylinder 52 advances distally into the opening 72 at the release zone of cylinder 52. Manual or automatic means, such as a spring-like member, or a push bar, may be provided to advance the next anchor to the release zone. The practitioner positions deployment device 50 adjacent the next section of suture 44 that the practitioner wants to secure with an anchor 10 and repeats the procedure until suture 44 is adequately anchored.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present invention.

Preferably, the various embodiments of the invention described herein will be processed before patient use. First, a new or used instrument, in this case, deployment device 50 and new anchors 10 are obtained and if necessary cleaned. The deployment device 50 and anchors 10 can then be sterilized by any suitable known sterilization technique. This can be done by any number of ways known to those skilled in the art including beta or gamma radiation, ethylene oxide, steam. In one sterilization technique, the deployment device 50 and anchors 10 are placed in a closed and sealed container, such as a plastic or TYVEK bag. The container and instruments are then placed in a field of radiation that can penetrate the container, such as gamma radiation, x-rays, or high-energy electrons. The radiation kills bacteria on the instruments and in the container. The sterilized instruments can then be stored in the sterile container. The sealed container keeps the deployment device and anchors sterile until it is opened in the medical facility.

The deployment device 50 and a plurality of anchors 10 can thus be provided as a sterile kit for use, for example, in a hospital or out patient facility. The kit may also include sutures. Alternatively, a plurality of anchors 10 may be provided in a kit for use with an existing deployment device.

In summary, numerous benefits are apparent which result from employing the concepts of the invention. The foregoing description of one or more embodiments of the invention has been presented for purposes of illustration and description. It is not intended to be exhaustive or to limit the invention to the precise form disclosed. Obvious modifications or variations are possible in light of the above teachings. The embodiments were chosen and described in order to best illustrate the principles of the invention and its practical application to thereby enable one of ordinary skill in the art to best utilize the invention in various embodiments and with various modifications as are suited to the particular use contemplated. It is intended that the scope of the invention be limited only by the claims appended hereto.

The invention claimed is:

1. A suture anchor for securing a section of a suture to patient tissue, comprising:
   a hollow member having an outer surface defining an enclosure, the member having a longitudinal axis and a slot through a portion of the outer surface in a direction transverse to the longitudinal axis, said slot providing an opening into the enclosure; and,
   a one-way valve positioned within said enclosure at said slot to allow entry of a suture through the slot and to prevent the exit of the suture from said enclosure;
   wherein the slot is configured such that it forms a cut through said hollow member at an angle relative to the longitudinal axis of the hollow member
   wherein said one-way valve is a resilient wire having a first end attached to a first surface within the enclosure and a second free end biased toward and contacting a second surface within the enclosure, said second surface of the enclosure facing and being spaced from the first surface of the enclosure, said second free end being positioned to span the slot at an apex of the slot thereof in a direction parallel to the longitudinal axis of the hollow member.

2. The suture anchor recited in claim 1 wherein said one-way valve is a leaf spring.

3. The suture anchor recited in claim 1 wherein the slot defines the apex and a pair of end sections.

4. The suture anchor recited in claim 1 wherein said hollow member is a cylinder.

5. A method for deploying a suture anchor to a section of suture in tissue not having an associated anchor, the method comprising:
   providing a deployment device comprising an elongate hollow member having a longitudinal axis, a distal end and a proximal end, a tip, a suture anchor release zone in said elongate member positioned adjacent and proximal to the tip, a launch bar having at least a portion thereof positioned in said release zone, said launch bar being movable within said release zone between a resting position and a launching position and being operatively connected to an actuation member positioned proximally to the elongate member, said hollow elongate member defining a housing for receiving a plurality of suture anchors in tandem along the longitudinal axis of the hollow member, each said suture anchor being configured for release from said release zone when such suture anchor is positioned within said release zone upon movement of said launch bar from said resting position to said launching position;
   providing the plurality of suture anchors in said housing of said hollow elongate member, each said suture anchor comprising a hollow member having an outer surface defining an enclosure therein, the hollow member having a longitudinal axis and a slot through a portion of the outer surface in a direction transverse to the longitudinal axis of the hollow member, said slot providing an opening into the enclosure, and a one-way valve positioned within said enclosure at said slot to allow entry of a suture through the opening into said enclosure and to prevent the exit of the suture from said enclosure, wherein the slot is configured such that it forms a cut through said hollow member at an angle relative to the longitudinal axis of the hollow member; and wherein said one-way valve is a resilient wire having a first end attached to a first surface within the enclosure and a second free end biased towards and contacting a second surface within the enclosure, said second surface of the enclosure facing and being spaced from the first surface of the enclosure, said second free end being positioned to span the slot at an apex of the slot thereof in a direction parallel to the longitudinal axis of the hollow member;
   advancing the distal end of the deployment device distally to the patient site;
   directing the tip of the deployment device under a section of suture and advancing the deployment device distally under the section of suture until the suture is over the slot and the suture anchor positioned in the release zone of the deployment device;

directing the deployment device to a position that slides the section of suture into the slot of the suture anchor, past the one-way valve to position the section of suture within the enclosure of the suture anchor;

moving the launch bar from the resting position to the launching position;

pushing the suture anchor out of the release zone; and, moving the deployment device in a proximal direction away from the suture anchor and the section of suture attached thereto.

6. The method recited in claim 5 wherein the step of advancing the deployment device to the patient site comprises inserting the deployment device into the proximal end of a channel leading to the patient site and advancing the deployment device distally through the channel to the patient site.

* * * * *